(12) United States Patent
Asano et al.

(10) Patent No.: US 9,663,541 B2
(45) Date of Patent: May 30, 2017

(54) GROUP 5 METAL OXO-ALKOXO COMPLEX, METHOD FOR PRODUCING SAME, AND METHOD FOR MANUFACTURING GROUP 5 METAL OXIDE FILM

(71) Applicants: TOSOH CORPORATION, Shunan-shi (JP); Sagami Chemical Research Institute, Ayase-shi (JP)

(72) Inventors: Sachio Asano, Kanagawa (JP); Tomoyuki Kinoshita, Kanagawa (JP); Yasushi Hara, Kanagawa (JP); Daiji Hara, Kanagawa (JP); Ryoji Tanaka, Kanagawa (JP); Ken-ichi Tada, Kanagawa (JP)

(73) Assignees: TOSOH CORPORATION, Shunan-shi (JP); Sagami Chemical Research Institute, Ayase-shi (JP)

( * ) Notice: Subject to any disclaimer, the term of this patent is extended or adjusted under 35 U.S.C. 154(b) by 173 days.

(21) Appl. No.: 14/758,142

(22) PCT Filed: Dec. 27, 2013

(86) PCT No.: PCT/JP2013/085248
§ 371 (c)(1),
(2) Date: Jun. 26, 2015

(87) PCT Pub. No.: WO2014/104358
PCT Pub. Date: Jul. 3, 2014

(65) Prior Publication Data
US 2015/0353588 A1 Dec. 10, 2015

(30) Foreign Application Priority Data
Dec. 28, 2012 (JP) .................................. 2012-286956

(51) Int. Cl.
*H01B 1/02* (2006.01)
*H01B 1/12* (2006.01)
(Continued)

(52) U.S. Cl.
CPC .............. *C07F 9/005* (2013.01); *C07C 29/68* (2013.01); *C07C 31/28* (2013.01); *C07C 33/26* (2013.01);
(Continued)

(58) Field of Classification Search
CPC ...... H01L 21/02175; C07F 9/005; C11D 7/08
(Continued)

(56) References Cited

U.S. PATENT DOCUMENTS

| 6,002,031 A | 12/1999 | Duncombe et al. |
| 2010/0035786 A1 | 2/2010 | Westwood |

FOREIGN PATENT DOCUMENTS

| JP | 2004-221239 A | 8/2004 |
| JP | 2007-182605 A | 7/2007 |
| JP | 2010-518242 A | 5/2010 |

OTHER PUBLICATIONS

Timothy J. Boyle, et al., "Niobium(V) Alkoxides. Synthesis. Structure, and Characterization of [Nb(.mu.-OCH2CH3)(OCH2C(CH3)3)4]2, {[H3CC(CH2O) (CH2-.mu.-O) (C(O)2) ] Nb2 (.mu.-O) (OCH2CH3) 5 }2, and { {H3CC (CH2O) 2 (CH2-.mu.-0) ] Nb (OCH2CH3)212 for Production of Mixed Metal Oxide Thin Films" Chemistry of Materials, XP008074156, 1997, pp. 3187-3198.
(Continued)

*Primary Examiner* — Khanh Tuan Nguyen
(74) *Attorney, Agent, or Firm* — Oblon, McClelland, Maier & Neustadt, L.L.P.

(57) ABSTRACT

A compound useful for the manufacture of a Group 5 metal oxide film is provided. The compound is a Group 5 metal
(Continued)

oxo-alkoxo complex represented by the following formula (A), and after preparing a film-forming material solution containing the compound and an organic solvent, a Group 5 metal oxide film can be manufactured using the film-forming material solution:

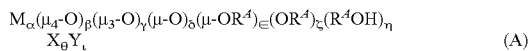

$$M_\alpha(\mu_4\text{-O})_\beta(\mu_3\text{-O})_\gamma(\mu\text{-O})_\delta(\mu\text{-OR}^4)_\in(OR^4)_\zeta(R^4OH)_\eta X_\theta Y_\iota \qquad (A)$$

(wherein M represents a niobium atom, etc.; $R^4$ represents an alkyl group; X represents an alkylenedioxy group; Y represents a carboxy group, etc.; α represents an integer of 3 to 10; β represents 0 or 1; γ represents an integer of 0 to 8; δ represents an integer of 2 to 9; ∈ represents an integer of 0 to 6; ζ represents an integer of 6 to 16; η represents an integer of 0 to 4; θ represents an integer of 0 to 2; and ι represents an integer of 0 to 6).

17 Claims, 6 Drawing Sheets

(51) Int. Cl.
| | | |
|---|---|---|
| C07F 9/00 | (2006.01) | |
| H01L 21/02 | (2006.01) | |
| C07C 29/68 | (2006.01) | |
| C07C 31/28 | (2006.01) | |
| C07C 33/26 | (2006.01) | |

(52) U.S. Cl.
CPC .......... *C07F 9/00* (2013.01); *H01L 21/02118* (2013.01); *H01L 21/02175* (2013.01); *H01L 21/02183* (2013.01); *H01L 21/02194* (2013.01); *H01L 21/02282* (2013.01); *H01L 21/02318* (2013.01)

(58) Field of Classification Search
USPC ...................................... 252/519.21; 510/176
See application file for complete search history.

(56) References Cited

OTHER PUBLICATIONS

International Search Report issued Mar. 25, 2014, in PCT/JP2013/085248, filed Dec. 27, 2013.
V. G. Kessler, et al., "The structure of $Nb_8O_{10}(OEt)_{20}$ and the nature of crystalline metal oxide alkoxides", Russian Journal of Inorganic Chemistry, 1991, vol. 36, No. 7, pp. 938-944.
Gulaim A. Seisenbaeva, et al., "Isolation, X-ray single crystal and theoretical study of quinquevalent metal oxoisopropoxide", $Nb_6O_8(^iPrO)_{14}(^iPrOH)_2$ and $Re_4O_6(O^iPr)_{10}$, Inorganica Chimica Acta, 2004, vol. 357, No. 2, pp. 468-474.
A. I. Yanovsky, et al., "Tantalum(v) oxoalkoxides. Synthesis and structure", Russian Chemical Bulletin, 1996, vol. 45, No. 1, pp. 115-121.
Isaac Abrahams, et al., "Polynuclear tantalum oxoalkoxides. Crystal structures of $[Ta_6O_{10}(OEt)_{20}]$, $[Ta_7O_9(OPr^1)_{17}]$ and $[Ta_5O_7(OBu^1)_{11}] C_6H_5Me$", Journal of the Chemical Society, Dalton Transactions, 2000, No. 16, pp. 2685-2691.
D. C. Bradley, et al., "The Structure of a Crystalline Niobium Oxide Ethoxide $Nb_8O_{10}(OEt)_{20}$", Chemical Communications (London), 1968, No. 18, pp. 1112-1113.
Mark Schormann, et al., "Preparation of bistrimethylsilylmethylniobiumtetrafluoride and the application of $KHF_2$ and $n$-$Bu_4NHF_2$ as fluorinating reagents", Journal of Organometallic Chemistry, 2001, vol. 621, No. 1-2, pp. 310-316.
Bee-Lean OOI, et al., "Synthesis and structure of cyclic hexanuclear-oxo-alkoxo-carboxylatoniobium(IV) complexes", Inorganica Chimica Acta, 2004, vol. 357, No. 2, pp. 625-629.
Nathalie Steunou, et al., "A Tetranuclear Niobium Oxo Acetate Complex. Synthesis, X-ray Crystal Structure, and Characterization by Solid-State and Liquid-State NMR Spectroscopy", Inorganic Chemistry, vol. 37, No. 5, pp. 901-910 (1998).
Leandra Herbst, et al., "*cyclo*-Tetra-μ-oxido-tetrakis[(acetylacetonato-$k_2$O,O)bis(ethanolato-$k$O)-niobium(V)]", Acta Crystallographica Section E: Structure Reports Online, 2011, vol. 67, No. 12, pp. m1669-sup10.
Liliane G. Hubert-Pfalzgraf, et al., "Niobium pinacolate complexes: synthesis and molecular structures of $Nb_3(\mu\text{-O})_2(\mu,n^2\text{-OCMe}_2CMe_2O)_2(n^2\text{—OCMe}_2CMe_2O)_4H$ and of $Nb_4(\mu\text{—O})_2(\mu_3\text{—O})_2(\mu, n^2\text{—OCMe}_2 CMe_2O)_2(OPr^1)_8$", 1999, vol. 18, No. 6, pp. 845-850.
Timothy J. Boyle, et al., "Crystallographic characterization of the esterification pathway of Group V alkoxides", Polyhedron, 2002, vol. 21, No. 23, pp. 2333-2345.
Silvia Gross, et al., "Cluster-Crosslinked Inorganic-Organic Hybrid Polymers: Influence of the Cluster Type on the Materials Properties", Materials Research Society Symposium Proceedings, 2002, vol. 726, Symposium Q, pp. 47-55.
Marck Schormann, et al., "Preparation of bistrimethylsilylmethylniobiumtetrafluoride and the application of $KHF_2$ and $n$-$Bu_4NHF_2$ as fluorinating reagents", Journal of Organometallic Chemistry, 2001, vol. 621, No. 1-2, pp. 310-316.
N. Ya. Turova, et al., "Tantalum(V) alkoxides: Electrochemical synthesis, mass-spectral investigation and oxoalkoxocomplexes", Polyhedron, 1996, vol. 15, No. 21, pp. 3869-3880.
Z. A. Starikova, et al., "Synthesis and structural study of polynuclear lithium oxoethoxo tantalates", Zhurnal Neorganicheskoi Khimii, 2003, vol. 48, No. 8, pp. 1275-1281.
Isaac Abrahams, et al., "Polynuclear tantalum oxoalkoxides. Crystal structures of $[Ta_8O_{10} (OEt)_{20}]$, $[Ta_7O_9 (OPr^1)_{17}]$ and $[Ta_5O_7 (OBu)_{11}] C_6H_5Me$", Dalton, 2000, No. 16, pp. 2685-2691.
Vernon C. Gibson, et al., "A novel tantalum butterfly oxo cluster, Journal of the Chemical Society, Chemical Communications", 1990, No. 1, (total 4 pages).
Combined Office Action and Search Report issued Apr. 19, 2016 in Chinese Patent Application No. 201380068922.X (with English language translation).
S.H. Mujawar, et al., "Electrochromic properties of spray-deposited niobium oxide thin films" Solid State Ionics, vol. 177, 2006, pp. 3333-3338.

GROUP 5 METAL OXO-ALKOXO COMPLEX, METHOD FOR PRODUCING SAME, AND METHOD FOR MANUFACTURING GROUP 5 METAL OXIDE FILM

TECHNICAL FIELD

The present invention relates to a Group 5 metal oxo-alkoxo complex useful as a material for the formation of a niobium oxide film or a tantalum oxide film, a method for producing the same, and a method for manufacturing a Group 5 metal oxide film using the Group 5 metal oxo-alkoxo complex.

BACKGROUND ART

A Group 5 metal oxide film such as niobium oxide and tantalum oxide is attracting attention as a film having a high refractive index and exhibiting high optical transparency, i.e., as a material for a device such as semiconductor device and optical device. The technique for manufacturing a Group 5 metal oxide film includes, in rough classification, two processes, i.e., a dry process and a wet process. The dry process includes a sputtering method, an ion plating method, an atomic layer deposition method (ALD method), a chemical vapor deposition method (CVD method), etc. The wet process includes a sol-gel method, an organic metal deposition method (Metal Organic Deposition; MOD method), etc. While the dry process requires a special production facility such as large vacuum apparatus, the wet process has a cost benefit in that the process can be performed only with a simple production facility. In the case of manufacturing a film by a wet process, the kind of the film-forming material and the film formation temperature greatly affect the quality of the film obtained. In Non-Patent Documents 1 to 12, a multinuclear niobium complex and a multinuclear tantalum complex, each having an oxo ligand and an alkoxy ligand, are described. The complexes described in those documents are different from the Group 5 metal oxo-alkoxo complex of the present invention in the number of central metals or the number of ligands. In addition, those documents are absolutely silent as to using the complex described in the documents as a film-forming material.

BACKGROUND ART DOCUMENT

Non-Patent Document

Non-Patent Document 1: Russian Journal of Inorganic Chemistry, Vol. 36, No. 7, page 938 (1991)
Non-Patent Document 2: Inorganica Chimica Acta, Vol. 357, No. 2, page 468 (2004)
Non-Patent Document 3: Russian Chemical Bulletin, Vol. 45, No. 1, page 115 (1996)
Non-Patent Document 4: Journal of the Chemical Society, Dalton Transactions, No. 16, page 2685 (2000)
Non-Patent Document 5: Chemical Communications (London), No. 18, page 1112 (1968)
Non-Patent Document 6: Journal of Organometallic Chemistry, Vol. 621, No. 1-2, page 310 (2001)
Non-Patent Document 7: Inorganica Chimica Acta, Vol. 357, No. 2, page 625 (2004)
Non-Patent Document 8: Inorganic Chemistry, Vol. 37, No. 5, page 901 (1998)
Non-Patent Document 9: Acta Crystallographica Section E: Structure Reports Online, Vol. 67, No. 12, page m1669 (2011)
Non-Patent Document 10: Polyhedron, Vol. 18, No. 6, page 845 (1999)
Non-Patent Document 11: Polyhedron, Vol. 21, No. 23, page 2333 (2002)
Non-Patent Document 12: Materials Research Society Symposium Proceedings, Vol. 726, Symposium Q, page 47 (2002)

SUMMARY OF INVENTION

Problem that Invention is to Solve

An object of the present invention is to develop a niobium complex and a tantalum complex, which are useful as a material capable of producing a Group 5 oxide film, specifically, a niobium oxide film or a tantalum oxide film, by a wet process at as low a temperature as possible, specifically, even at a temperature of about 200° C. or less, and a method for producing the same.

Means for Solving Problem

As a result of intensive studies to solve those problems, the present inventors have found that a Group 5 metal oxo-alkoxo complex represented by formula (1), chemical formula (3), chemical formula (4) or chemical formula (5) is an excellent material for attaining the above-described object. The present invention has been accomplished based on this finding.

That is, the present invention relates to a Group 5 metal oxo-alkoxo complex represented by formula (1), chemical formula (3), chemical formula (4) or chemical formula (5):

$$M_A(\mu_4\text{-O})_B(\mu_3\text{-O})_C(\mu\text{-O})_D(\mu\text{-O}^t\text{Bu})_E(\text{O}^t\text{Bu})_F \quad (1)$$

(wherein M represents a niobium atom or a tantalum atom; and A, B, C, D, E and F represent respectively numerical values of 10, 1, 8, 8, 0 and 16 or of 9, 1, 5, 9, 1 and 14):

[Chem. 1]

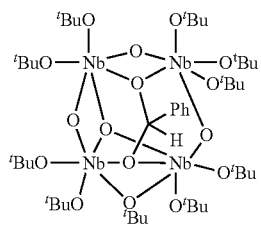

(3)

[Chem. 2]

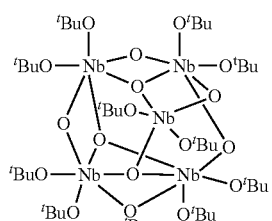

(4)

[Chem. 3]

-continued

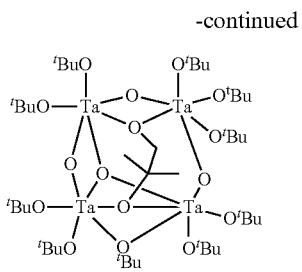

(5)

Effects of Invention

The Group 5 metal oxo-alkoxo complex of the present invention can be used as a film-forming material, and by using this film-forming, a Group 5 metal oxide film can be manufactured at a low temperature of about 200° C.

MODE FOR CARRYING OUT INVENTION

Figure 1:
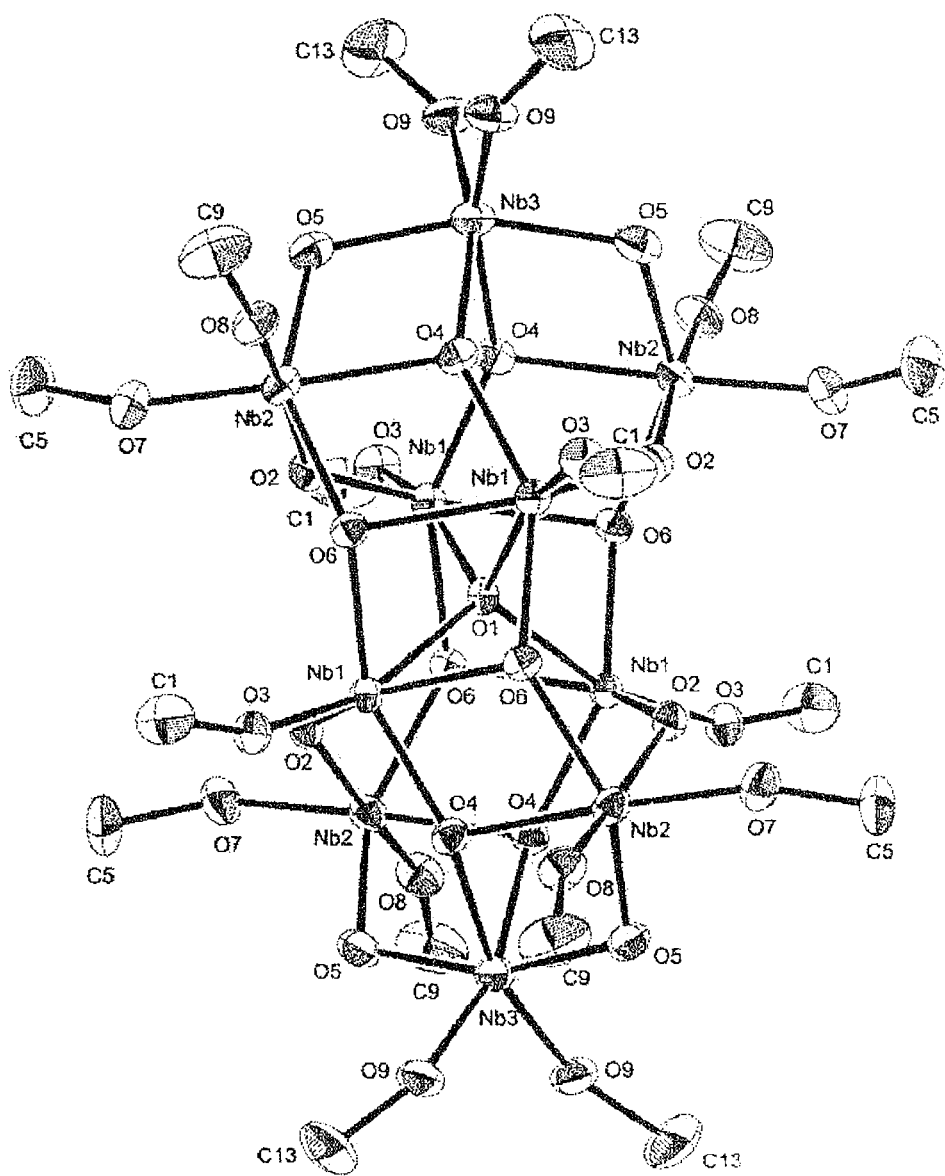
FIG. 1 is a view showing the molecular structure as the result of single-crystal X-ray structure analysis of the crystal obtained in Example 1; in the Figure, the depiction of the terminal methyl group of a tert-butyloxy group, the diisopropyl ether molecule as a crystallization solvent, and all hydrogen atoms is omitted.

The present invention is described below.

In the description of the present invention, Ph, Me, Et, Pr, $^{i}$Pr, $^{c}$Pr, Bu, $^{i}$Bu, $^{s}$Bu, $^{t}$Bu, $^{c}$Bu, Pe, $^{i}$Pe, Np, $^{t}$Pe, $^{c}$Pe, Hx, $^{i}$Hx, $^{c}$Hx, Hp, Oct, Non, $^{t}$Oct, Dec, Ad, Und and Dod stand for a phenyl group, a methyl group, an ethyl group, a propyl group, an isopropyl group, a cyclopropyl group, a butyl group, an isobutyl group, a sec-butyl group, a tert-butyl group, a cyclobutyl group, a pentyl group, an isopentyl group, a neopentyl group, a tert-pentyl group, a cyclopentyl group, a hexyl group, an isohexyl group, a cyclohexyl group, a heptyl group, an octyl group, a nonyl group, a 1,1,3,3-tetramethylbutyl group, a decyl group, an adamantyl group, au undecyl group and a dodecyl group, respectively.

Of Group 5 metal oxo-alkoxo complexes represented by formula (1), chemical formula (3), chemical formula (4) and chemical formula (5), first, the Group 5 metal oxo-alkoxo complex represented by formula (1) is described in detail.

The Group 5 metal oxo-alkoxo complex represented by formula (1) (Group 5 metal oxo-alkoxo complex (1)) of the present invention includes hexadecakis(tert-butyloxo)($\mu_4$-oxo)octakis($\mu_3$-oxo)octakis($\mu$-oxo)decaniobium (Nb$_{10}$($\mu_4$-O)($\mu_3$-O)$_8$($\mu$-O)$_8$(O$^t$Bu)$_{16}$), hexadecakis(tert-butyloxo)($\mu_4$-oxo)octakis($\mu_3$-oxo)octakis($\mu_3$-oxo)decatantalum (Ta$_{10}$($\mu_4$-O)($\mu_3$-O)$_8$($\mu$-O)$_8$(O$^t$Bu)$_{16}$), ($\mu$-tert-butyloxo)tetradecakis(tert-butyloxo)($\mu_4$-oxo)pentakis($\mu_3$-oxo)nonakis($\mu$-oxo)nonaniobium (Nb$_9$($\mu_4$-O)($\mu_3$-O)$_5$($\mu$-O)$_9$($\mu$-O$^t$Bu)(O$^t$Bu)$_{14}$), and ($\mu$-tert-butyloxo)tetradecakis(tert-butyloxo)($\mu_4$-oxo)pentakis($\mu_3$-oxo)nonakis($\mu$-oxo)nonatantalum (Ta$_9$($\mu_4$-O)($\mu_3$-O)$_5$($\mu$-O)$_9$($\mu$-O$^t$Bu)(O$^t$Bu)$_{14}$). In the description of the present invention, Nb$_{10}$($\mu_4$-O)($\mu_3$-O)$_8$($\mu$-O)$_8$(O$^t$Bu)$_{16}$ and T$_{10}$($\mu_4$-O)($\mu_3$-O)$_8$($\mu$-O)$_8$(O$^t$Bu)$_{16}$ are a Group 5 metal oxo-alkoxo complex represented by formula (1A):

[Chem. 4]

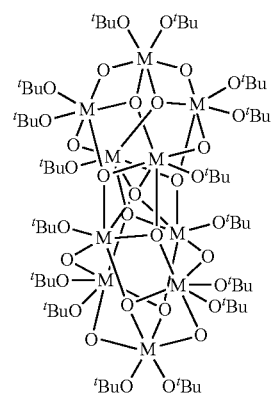

(1A)

(wherein M has the same meaning as above), and Nb$_9$($\mu_4$-O)($\mu_3$-O)$_5$($\mu$-O)$_9$($\mu$-O$^t$Bu)(O$^t$Bu)$_{14}$ and Ta$_9$($\mu_4$-O)($\mu_3$-O)$_5$($\mu$-O)$_9$($\mu$-O$^t$Bu)(O$^t$Bu)$_{14}$ are a Group 5 metal oxo-alkoxo complex represented by formula (1B):

[Chem. 5]

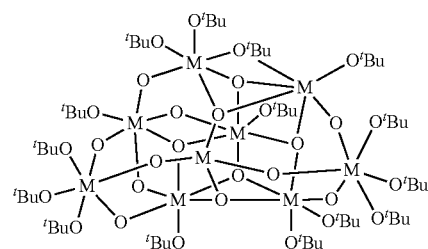

(1B)

(wherein M has the same meaning as above).

The method for producing the Group 5 metal oxo-alkoxo complex (1) of the present invention is described below. The Group 5 metal oxo-alkoxo complex (1) of the present invention can be produced according to the following production methods 1 to 5.

Production method 1 of the present invention is a method of reacting a metal imido-trialkoxo complex (2) with an oxidant to produce the Group 5 metal oxo-alkoxo complex (1) of the present invention.

Production Method 1:

[Chem. 6]

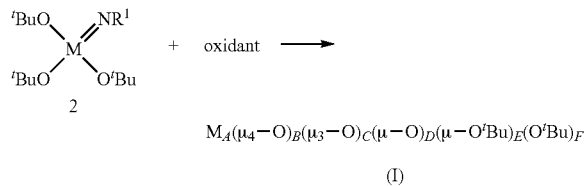

$$M_A(\mu_4-O)_B(\mu_3-O)_C(\mu-O)_D(\mu-O^tBu)_E(O^tBu)_F$$

(I)

(wherein $R^1$ represents a $C_4$-$C_{12}$ tertiary alkyl group or a phenyl group represented by formula (2Ar):

[Chem. 7]

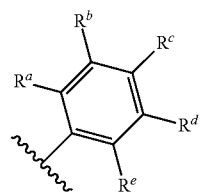

(2Ar)

(wherein each of $R^a$, $R^b$, $R^c$, $R^d$ and $R^e$ independently represents a hydrogen atom or a $C_1$-$C_6$ alkyl group), which may be substituted; and M, A, B, C, D, E and F have the same meanings as above).

First, the method for obtaining the metal imido-trialkoxo complex (2) used as a raw material for synthesis in production method 1 of the present invention is described. In the case where $R^1$ of the metal imido-trialkoxo complex (2) is a $C_4$-$C_{12}$ tertiary alkyl group, the complex can be produced according to the method described in JP-A-2008-266280 (the term "JP-A" as used herein means an "unexamined published Japanese patent application"). In the case where $R^1$ is a phenyl group (2Ar) that may be substituted, the complex can be produced according to the following production method Ar. Production method Ar is a method of reacting a metal imido-trialkoxo complex (2a) with an aniline derivative (6) to produce a metal imido-trialkoxo complex (2b).

Production Method Ar:

[Chem. 7]

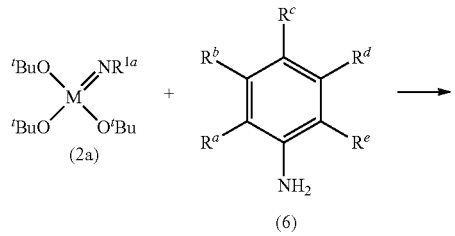

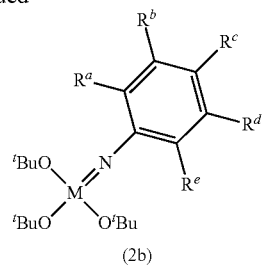

(2b)

(wherein $R^{1a}$ represents a $C_1$-$C_{12}$ alkyl group; and M, $R^a$, $R^b$, $R^c$, $R^d$ and $R^e$ have the same meanings as above).

The metal imido-trialkoxo complex (2a) used as a raw material for synthesis in production method Ar can be produced according to the method described in JP-A-2008-266280.

Definitions of $R^1$, $R^{1a}$, $R^a$, $R^b$, $R^c$, $R^d$ and $R^e$ are described in detail below. Specific examples of the $C_4$-$C_{12}$ tertiary alkyl group represented by $R^1$ include a tert-butyl group, a tert-pentyl group, a 1,1-dimethylbutyl group, a 1-ethyl-1-methylpropyl group, a 1,1,2-trimethylpropyl group, a 1,1-dimethylpentyl group, a 1,1-diethylpropyl group, a 1-ethyl-1-methylbutyl group, a 1,1,2-trimethylbutyl group, a 1,1,3-trimethylbutyl group, a 1,1,2,2-tetramethylpropyl group, a 1,1-dimethylhexyl group, a 1,1-diethylbutyl group, a 1-methyl-1-propylbutyl group, a 1-ethyl-1-methylpentyl group, a 1,1,3,3-tetramethylbutyl group, a 1,1-dimethylheptyl group, a 1,1-diethylpentyl group, a 1,1,3,3-tetramethylpentyl group, a 1,1,2,3,3-pentamethylbutyl group, a 1,1-dimethyloctyl group, a 1,1-diethylhexyl group, a 1,1-dimethylnonyl group, a 1,1-diethylheptyl group, a 1,1-dimethyldecyl group, and a 1,1-diethyloctyl group.

The $C_1$-$C_{12}$ alkyl group represented by $R^{1a}$ may be any of a linear alkyl group, a branched alkyl group, and a cyclic alkyl group. Specific examples thereof include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, a cyclobutylmethyl group, a heptyl group, a cyclohexylmethyl group, a 1,1-diethyl-propyl group, a 2-methylcyclohexyl group, a 4-methylcyclohexyl group, an octyl group, a 2,5-dimethylcyclohexyl group, a 3,5-dimethylcyclohexyl group, a 1,1,3,3-tetramethylbutyl group, a nonyl group, a 1,1,2,3,3-pentamethylbutyl group, a decyl group, a 1,1-diethyl-3,3-dimethylbutyl group, an adamantyl group, a 1,1-dimethyloctyl group, a 1,1-dipropylbutyl group, an undecyl group, a dodecyl group, a 1,1-dimethyldecyl group, and a 1,1-diethyloctyl group.

The $C_1$-$C_6$ alkyl group represented by $R^a$, $R^b$, $R^c$, $R^d$ and $R^e$ may be any of a linear alkyl group, a branched alkyl group and a cyclic alkyl group, and specific examples thereof include a methyl group, an ethyl group, a propyl group, an isopropyl group, a cyclopropyl group, a butyl group, an isobutyl group, a sec-butyl group, a tert-butyl group, a cyclobutyl group, a cyclopropylmethyl group, a pentyl group, an isopentyl group, a neopentyl group, a tert-pentyl group, a 1-methylbutyl group, a 2-methylbutyl group, a 1,2-dimethylpropyl group, a 1-ethylpropyl group, a cyclopentyl group, a cyclobutylmethyl group, a cyclopropylethyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, and a cyclohexyl group. Specific examples of the phenyl group (2Ar) that may be substituted include a phenyl group, a 2-methylphenyl group, and a 4-tert-butylphenyl group.

As the metal imido-trialkoxo complex (2) which can be used as a raw material in production method 1 of the Group 5 metal oxo-alkoxo complex of the present invention, (tert-butylimido)tri(tert-butyloxo)niobium, (tert-pentylimido)tri(tert-butyloxo)niobium, (1,1,3,3-tetramethylbutylimido)tri(tert-butyloxo)niobium, (phenylimido)tri(tert-butyloxo)niobium, (tert-butylimido)tri(tert-butyloxo)tantalum, (1,1,3,3-tetramethylbutylimido)tri(tert-butyloxo)tantalum and (phenylimido)tri(tert-butyloxo)tantalum are preferred from the standpoint that the Group 5 metal oxo-alkoxo complex of the present invention can be produced in a high yield.

The kind of the oxidant is described below. Oxidants that can be used in production method 1 of the present invention are oxygen, air and ozone. Of these oxidants, one kind may be used alone, or two or more kinds may be mixed in an arbitrary ratio and used. From the standpoint that the yield of the Group 5 metal oxo-alkoxo complex (1) of the present invention is high, oxygen and air are preferably used, and oxygen is more preferred.

As to the molar ratio between the metal imido-trialkoxo complex (2) and the oxidant in production method 1 of the present invention, in view of high yield, an equimolar or greater amount of oxidant is preferably reacted per mol of metal imido-trialkoxo complex (2). In the case where the oxidant is oxygen or air and the pressure inside the reaction vessel is from 0.1 to 0.2 MPa, it is more preferable to react the oxidant in an amount of 5 times by mol or more per mol of metal imido-trialkoxo complex (2). In the case where the oxidant is oxygen or air and the pressure inside the reaction vessel is 0.2 MPa or more, it is more preferable to react the oxidant in an amount ranging from equimolar to less than 5 times by mol per mol of metal imido-trialkoxo complex (2). The oxidant may be diluted, if desired, with an inert gas such as helium, neon, argon, krypton, xenon and nitrogen. From the standpoint that production method 1 of the present invention can be safely performed, the oxidant is preferably used by diluting it with an inert gas. In the case of using the oxidant by diluting it, the mixing ratio between the oxidant and the inert gas is not particularly limited, and these may be mixed in an arbitrary ratio. From the standpoint that the yield of the Group 5 metal oxo-alkoxo complex (1) of the present invention is high, the volume ratio of oxidant:inert gas is preferably from 1:99 to 99:1, more preferably from 20:80 to 80:20.

The pressure inside the reaction vessel in production method 1 of the present invention is not particularly limited and is appropriately selected preferably from the range of 0.1 to 1 MPa, more preferably from the range of 0.1 to 0.7 MPa, whereby the Group 5 metal oxo-alkoxo complex of the present invention can be produced in a high yield.

In production method 1 of the present invention, either a Group 5 metal oxo-alkoxo complex (1A) or a Group 5 metal oxo-alkoxo complex (1B) can be preferentially produced by appropriately selecting the reaction temperature and the molar ratio between the metal imido-trialkoxo complex (2) and the oxidant.

Specifically, in a preferred embodiment, the reaction temperature is from 140 to 160° C. and as to the molar ratio between the metal imido-trialkoxo complex (2) and the oxidant, an oxidant in an amount ranging from equimolar to less than 1.5 mol is reacted per mol of metal imido-trialkoxo complex (2), whereby the Group 5 metal oxo-alkoxo complex (1A) of the present invention can be preferentially produced.

In another preferred embodiment, the reaction temperature is from 100 to 120° C. and as to the molar ratio between the metal imido-trialkoxo complex (2) and the oxidant, an oxidant in an amount ranging from equimolar to less than 3 mol is reacted per mol of metal imido-trialkoxo complex (2); or the reaction temperature is from 140 to 160° C. and as to the molar ratio between the metal imido-trialkoxo complex (2) and the oxidant, an oxidant in an amount ranging from 3 mol to less than 5 mol is reacted per mol of metal imido-trialkoxo complex (2); whereby the Group 5 metal oxo-alkoxo complex (1B) of the present invention can be preferentially produced.

Production method 1 can be performed either in an organic solvent or under solvent-free conditions. From the standpoint that the yield of the Group 5 metal oxo-alkoxo complex (1) of the present invention is high, the production method 1 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (1) of the present invention, an aliphatic hydrocarbon such as hexane and heptane, and an aromatic hydrocarbon such as toluene and xylene, are preferred. In the case of using an organic solvent in production method 1, the amount of the organic solvent used is not particularly limited, and the organic solvent is used in an appropriately selected amount, whereby the Group 5 metal oxo-alkoxo complex (1) of the present invention can be produced in a high yield.

From the standpoint that the yield of the Group 5 metal oxo-alkoxo complex (1) of the present invention is high, the reaction temperature in production method 1 of the present invention is preferably from 80 to 350° C., more preferably from 80 to 200° C.

The reaction time is not particularly limited and when the pressure inside the reaction vessel is less than 0.2 MPa, the reaction time is appropriately selected from the range of preferably from 1 to 30 days, more preferably from 5 to 20 day, or when the pressure inside the reaction vessel is 0.2 MPa or more, the reaction time is appropriately selected from the range of preferably from 1 to 48 hours, more preferably from 1 to 32 hours, whereby the Group 5 metal oxo-alkoxo complex (1) of the present invention can be produced in a high yield.

The Group 5 metal oxo-alkoxo complex (1) of the present invention produced by production method 1 may be purified, if desired, by appropriately using a general purification method such as filtration, extraction, distillation, sublimation, precipitation and crystallization.

Production method 2 of the present invention is described below. Production method 2 of the present invention is a method of reacting a metal imido-trialkoxo complex (2a) and an aniline derivative (6) with an oxidant to produce the Group 5 metal oxo-alkoxo complex (1) of the present invention.

Production Method 2:

[Chem. 8]

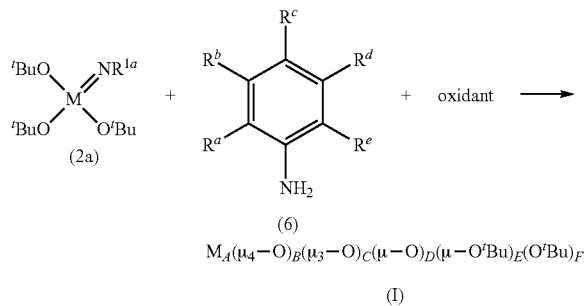

$M_A(\mu_4-O)_B(\mu_3-O)_C(\mu-O)_D(\mu-O^tBu)_E(O^tBu)_F$ (I)

(wherein M, $R^{1a}$, $R^a$, $R^b$, $R^c$, $R^d$, $R^e$, A, B, C, D, E and F have the same meanings as above.)

Production method 2 of the present invention has the same meaning as simultaneously performing production method 1 and production method Ar in combination and is performed under the same conditions as in production method 1 and production method Ar, whereby the Group 5 metal oxo-alkoxo complex (1) of the present invention can be produced.

The aniline derivative (6) specifically includes, for example, aniline, o-toluidine, and 4-tert-butylaniline.

Production method 3 of the present invention is described below. Production method 3 of the present invention is a method of heating a Group 5 metal oxo-alkoxo complex represented by chemical formula (3) to produce the Group 5 metal oxo-alkoxo complex (1-Nb) of the present invention.

Production Method 3:

[Chem. 9]

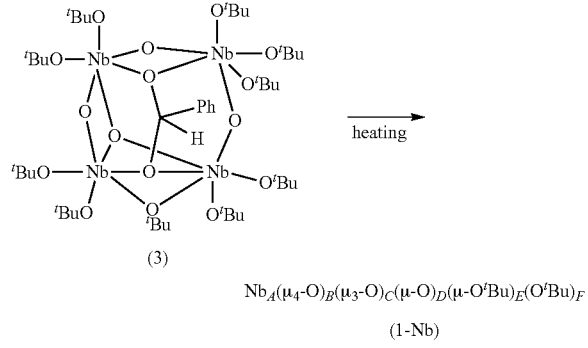

$Nb_A(\mu_4-O)_B(\mu_3-O)_C(\mu-O)_D(\mu-O^tBu)_E(O^tBu)_F$ (1-Nb)

(wherein A, B, C, D, E and F have the same meanings as above.)

The Group 5 metal oxo-alkoxo complex (3) used as a raw material for synthesis in production method 3 of the present invention can be produced according to production method 6 described later.

From the standpoint that the yield of the Group 5 metal oxo-alkoxo complex (1-Nb) of the present invention is high, the reaction temperature in production method 3 of the Group 5 metal oxo-alkoxo complex (1-Nb) of the present invention is preferably from 50 to 350° C., more preferably from 80 to 200° C., still more preferably from 100 to 180° C. In this connection, a Group 5 metal oxo-alkoxo complex (1A-Nb) can be preferentially synthesized in the range from 120 to 145° C., and a Group 5 metal oxo-alkoxo complex (1B-Nb) can be preferentially synthesized in the range from 145 to 160° C. The Group 5 metal oxo-alkoxo complex (1A-Nb) and the Group 5 metal oxo-alkoxo complex (1B-Nb) are, respectively, complexes where M in formula (1A) and formula (1B) is Nb.

The reaction time is not particularly limited and is appropriately selected from the range of preferably from 1 to 48 hours, more preferably from 6 to 24 hours, whereby the Group 5 metal oxo-alkoxo complex (1-Nb) of the present invention can be produced in a high yield.

Production method 3 can be performed either in an organic solvent or under solvent-free conditions. From the standpoint that the yield of the Group 5 metal oxo-alkoxo complex (1-Nb) of the present invention is high, the production method 3 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, mesitylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (1-Nb) of the present invention, hexane, heptane, toluene, xylene and mesitylene are preferred. In the case of using an organic solvent in production method 3, the amount of the organic solvent used is not particularly limited, and the organic solvent is used in an appropriately selected amount, whereby the Group 5 metal oxo-alkoxo complex (1-Nb) of the present invention can be produced in a high yield.

The Group 5 metal oxo-alkoxo complex (1-Nb) of the present invention produced by production method 3 may be purified, if desired, by appropriately using a general purification method such as filtration, extraction, distillation, sublimation, precipitation and crystallization.

Production method 4 of the present invention is described below. Production method 4 of the present invention is a method of heating a Group 5 metal oxo-alkoxo complex (4) to produce the Group 5 metal oxo-alkoxo complex (1-Nb).

Production Method 4:

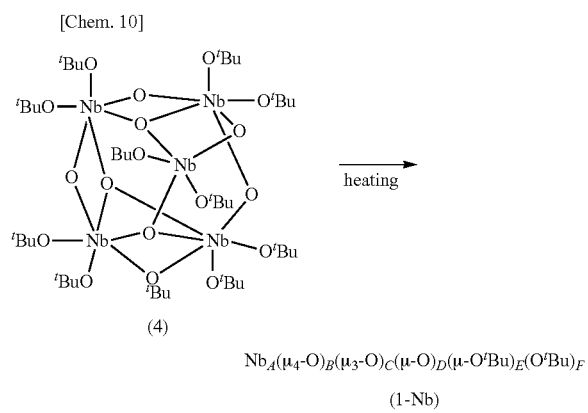

(wherein A, B, C, D, E and F have the same meanings as above.)

The Group 5 metal oxo-alkoxo complex (4) used as a raw material for synthesis in production method 4 of the present invention can be produced according to production method 7 or 8 described later.

From the standpoint that the yield of the Group 5 metal oxo-alkoxo complex (1-Nb) of the present invention is high, the reaction temperature in production method 4 of the Group 5 metal oxo-alkoxo complex (1-Nb) of the present invention is preferably from 50 to 350° C., more preferably from 80 to 200° C., still more preferably from 100 to 180° C.

The reaction time is not particularly limited and is appropriately selected from the range of preferably from 1 to 48 hours, more preferably from 1 to 24 hours, whereby the Group 5 metal oxo-alkoxo complex (1-Nb) of the present invention can be produced in a high yield.

Production method 4 can be performed either in an organic solvent or under solvent-free conditions. From the standpoint that the yield of the Group 5 metal oxo-alkoxo complex (1-Nb) of the present invention is high, the production method 4 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, mesitylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (1-Nb) of the present invention, hexane, heptane, toluene, xylene and mesitylene are preferred. In the case of using an organic solvent in production method 4, the amount of the organic solvent used is not particularly limited, and the organic solvent is used in an appropriately selected amount, whereby the Group 5 metal oxo-alkoxo complex (1-Nb) of the present invention can be produced in a high yield.

The Group 5 metal oxo-alkoxo complex (1-Nb) of the present invention produced by production method 4 may be purified, if desired, by appropriately using a general purification method such as filtration, extraction, distillation, sublimation, precipitation and crystallization.

Production method 5 of the present invention is described below. Production method 5 of the present invention is a method of reacting pentakis(tert-butyloxo)niobium (Nb(O$^t$Bu)$_5$) with diacetone alcohol in a molar ratio of 1.3 to 2.0 mol of diacetone alcohol per mol of pentakis(tert-butyloxo)niobium to produce the Group 5 metal oxo-alkoxo complex (1B-Nb) of the present invention.

Production Method 5:

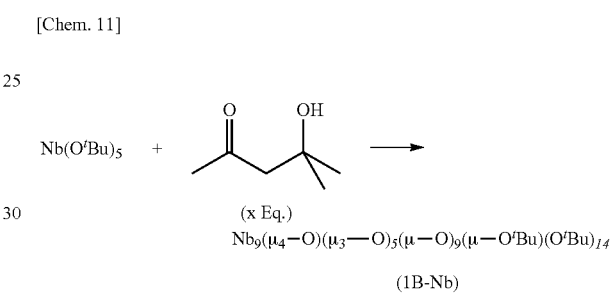

(wherein x represents a numerical value of 1.3 to 2.0.)

The pentakis(tert-butyloxo)niobium used as a raw material for synthesis in production method 5 of the present invention can be produced according to production method Nb1 described below. Production method Nb1 is a method of reacting a metal imido-trialkoxo complex (2a-Nb) with a tert-butyl alcohol to produce the pentakis(tert-butyloxo)niobium.

Production Method Nb1:

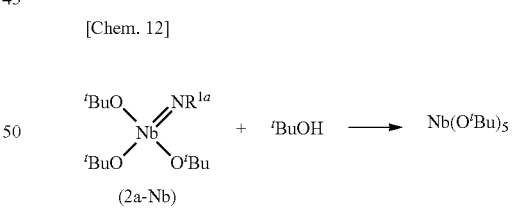

(wherein R$^{1a}$ has the same meaning as above.)

The molar ratio between the pentakis(tert-butyloxo)niobium and the diacetone alcohol in production method 5 of the Group 5 metal oxo-alkoxo complex (1B-Nb) of the present invention is limited to the range of 1.3 to 2.0 mol per mol of pentakis(tert-butyloxo)niobium, and from the standpoint that the yield of the Group 5 metal oxo-alkoxo (1B-Nb) of the present invention is high, from 1.6 to 1.8 mol of diacetone alcohol is preferably reacted per mol of pentakis(tert-butyloxo)niobium.

The reaction temperature in production method 5 of the present invention is not particularly limited, and in view of high yield of the Group 5 metal oxo-alkoxo complex (1B-

Nb) of the present invention, the reaction temperature is preferably from −80° C. to 350° C., more preferably from −20° C. to 200° C., still more preferably from 0 to 100° C.

The reaction time is not particularly limited and is appropriately selected from the range of preferably from 1 minute to 10 days, more preferably from 1 to 24 hours, whereby the Group 5 metal oxo-alkoxo complex (1B-Nb) of the present invention can be produced in a high yield.

Production method 5 can be performed either in an organic solvent or under solvent-free conditions. From the standpoint that the yield of the Group 5 metal oxo-alkoxo complex (1B-Nb) of the present invention is high, the production method 5 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, mesitylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (1B-Nb) of the present invention, hexane, heptane, toluene, xylene and mesitylene are preferred. In the case of using an organic solvent in production method 5, the amount of the organic solvent used is not particularly limited, and the organic solvent is used in an appropriately selected amount, whereby the Group 5 metal oxo-alkoxo complex (1B-Nb) of the present invention can be produced in a high yield.

The Group 5 metal oxo-alkoxo complex (1B-Nb) of the present invention produced by production method 5 may be purified, if desired, by appropriately using a general purification method such as filtration, extraction, distillation, sublimation, precipitation and crystallization.

The Group 5 metal oxo-alkoxo complex of the present invention represented by chemical formula (3) (Group 5 metal oxo-alkoxo complex (3)) or chemical formula (4) (Group 5 metal oxo-alkoxo complex (4)) is described in detail below.

Figure 4:
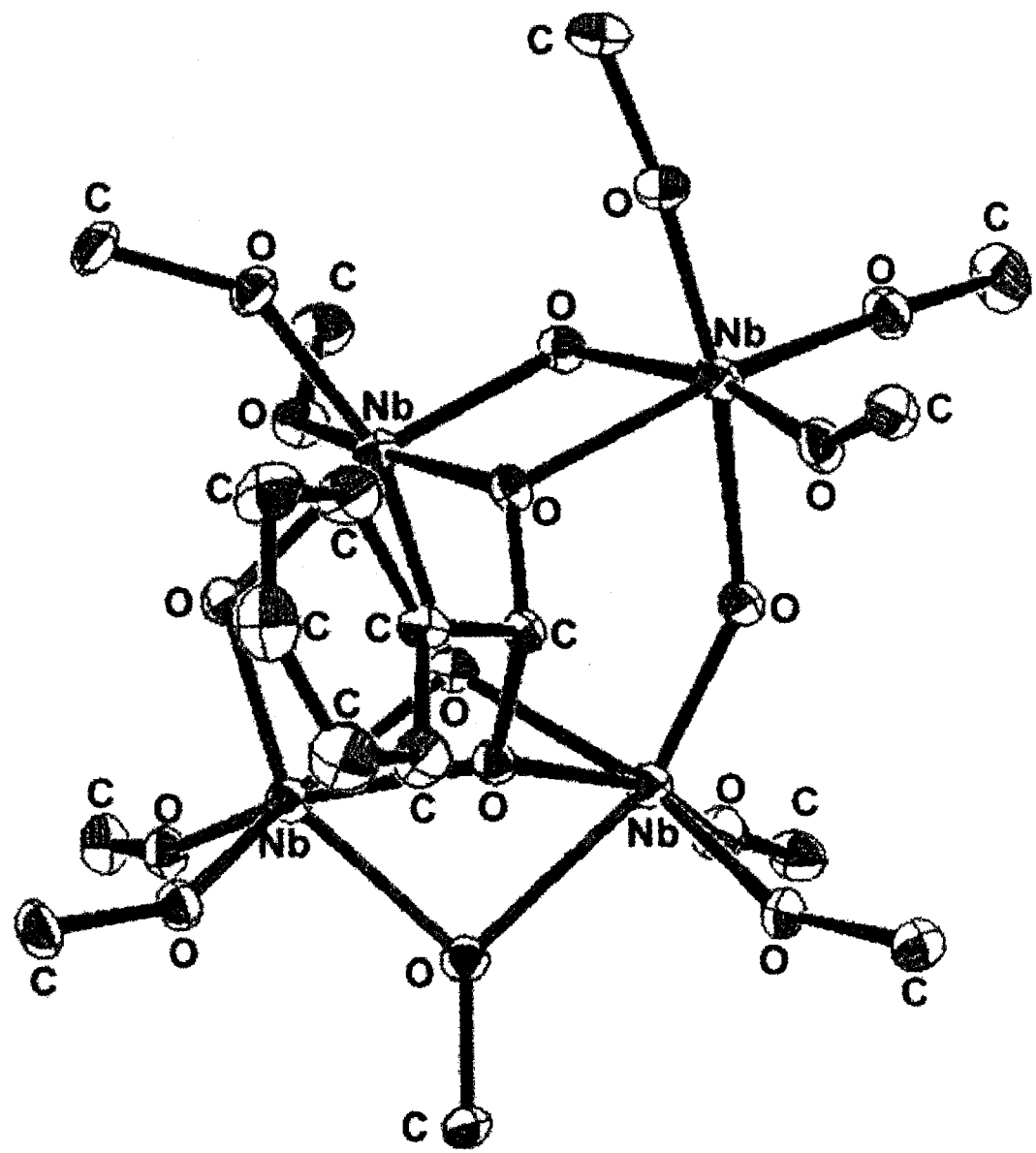
FIG. 4 is a view showing the molecular structure as the result of single-crystal X-ray structure analysis of the crystal obtained in Example 26; in the Figure, the depiction of the terminal methyl group of a tert-butyloxy group and all hydrogen atoms is omitted.
Figure 5:
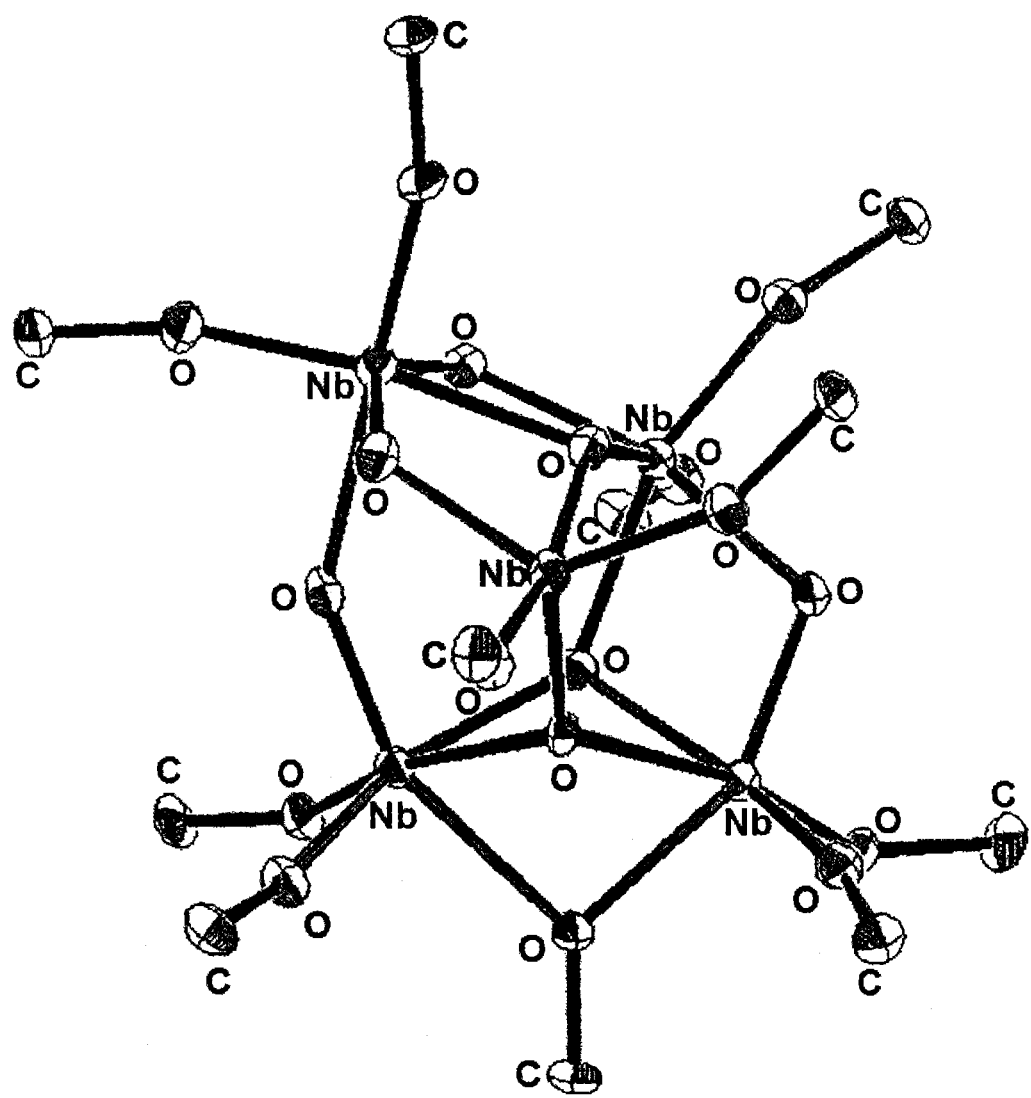
FIG. 5 is a view showing the molecular structure as the result of single-crystal X-ray structure analysis of the crystal obtained in Example 28; in the Figure, the depiction of the terminal methyl group of a tert-butyloxy group and all hydrogen atoms is omitted.

The Group 5 metal oxo-alkoxo complexes of the present invention represented by chemical formula (3) and chemical formula (4) have molecular structures depicted in the later-described FIG. 4 and FIG. 5, respectively.

The Group 5 metal oxo-alkoxo complex (3) of the present invention has a pair of geometric isomers based on the difference in the benzylidene dioxo ligand orientation, and the present invention encompasses both isomers.

The production methods of the Group 5 metal oxo-alkoxo complexes (3) and (4) of the present invention are described below. The Group 5 metal oxo-alkoxo complex (3) of the present invention can be produced according to the following production method 6, and the Group 5 metal oxo-alkoxo complex (4) can be produced according to production method 7 or 8 described later.

Production method 6 is described. Production method 6 of the present invention is a method of reacting a metal imido-trialkoxo complex (2a-Nb) with benzaldehyde to produce the Group 5 metal oxo-alkoxo complex (3) of the present invention.

Production Method 6:

[Chem. 13]

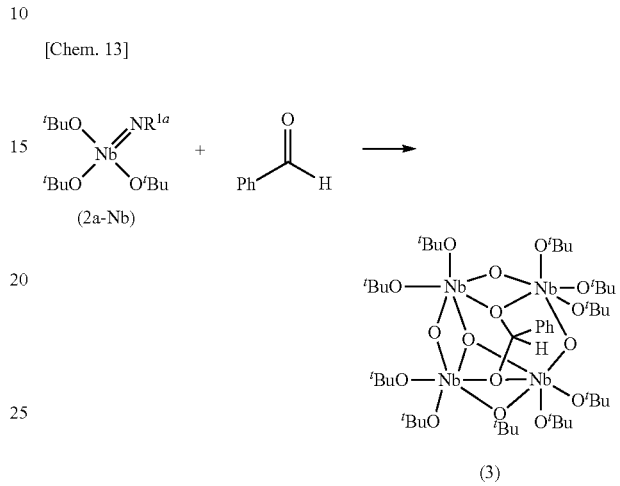

(wherein $R^{1a}$ has the same meaning as above.)

As for the $C_1$-$C_{12}$ alkyl group represented by $R^{1a}$, from the standpoint that the yield of the Group 5 metal oxo-alkoxo complex (3) of the present invention is high, $R^{1a}$ is preferably a $C_4$-$C_8$ alkyl group, more preferably a tert-butyl group.

The metal imido-trialkoxo complex (2a-Nb) used as a raw material for synthesis in production method 6 of the present invention can be produced according to the method described in JP-A-2008-266280.

As the metal imido-trialkoxo complex (2a-Nb), from the standpoint that the yield of the Group 5 metal oxo-alkoxo complex (3) of the present invention is high, (butylimido)tri(tert-butyloxo)niobium (Nb(NBu)(O$^t$Bu)$_3$), (isobutylimido)tri(tert-butyloxo)niobium (Nb(N$^i$Bu)(O$^t$Bu)$_3$), (sec-butylimido)tri(tert-butyloxo)niobium (Nb(NNp)(O$^t$Bu)$_3$), (tert-butylimido)tri(tert-butyloxo)niobium (Nb(N$^t$Bu)(O$^t$Bu)$_3$), (pentylimido)tri(tert-butyloxo)niobium (Nb(NPe)(O$^t$Bu)$_3$), (isopentylimido)tri(tert-butyloxo)niobium (Nb(N-Pe)(O$^t$Bu)$_3$), (neopentylimido)tri(tert-butyloxo)niobium (Nb(NNp)(O$^t$Bu)$_3$), (tert-pentylimido)tri(tert-butyloxo)niobium (Nb(N$^t$Pe)(O$^t$Bu)$_3$), (1-methylbutylimido)tri(tert-butyloxo)niobium (Nb(NCHMePr)(O$^t$Bu)$_3$), (2-methylbutylimido)tri(tert-butyloxo)niobium (Nb(NCH$_2$CHEtMe)(O$^t$Bu)$_3$), (1,2-dimethylpropylimido)tri(tert-butyloxo)niobium (Nb(NCHMeCHMe$_2$)(O$^t$Bu)$_3$), (hexylimido)tri(tert-butyloxo)niobium (Nb(NHx)(O$^t$Bu)$_3$), (isohexylimido)tri(tert-butyloxo)niobium (Nb(N$^i$Hx)(O$^t$Bu)$_3$), (1-methylpentylimido)tri(tert-butyloxo)niobium (Nb(NCHMeBu)(O$^t$Bu)$_3$), (2-methylpentylimido)tri(tert-butyloxo)niobium (Nb(NCH$_2$CHMePr)(O$^t$Bu)$_3$), (3-methylpentylimido)tri(tert-butyloxo)niobium (Nb(NCH$_2$CH$_2$CHMeEt)(O$^t$Bu)$_3$), (1,1-dimethylbutylimido)tri(tert-butyloxo)niobium (Nb(NCMe$_2$Pr)(O$^t$Bu)$_3$), (1,2-dimethylbutylimido)tri(tert-butyloxo)niobium (Nb(NCHMeCHMeEt)(O$^t$Bu)$_3$), (2,2-dimethylbutylimido)tri(tert-butyloxo)niobium (Nb(NCH$_2$CMe$_2$Et)(O$^t$Bu)$_3$), (1,3-dimethylbutylimido)tri(tert-butyloxo)niobium (Nb(NCHMeCH$_2$CHMe$_2$)(O$^t$Bu)$_3$), (2,3-dimethylbutylimido)tri(tert-butyl oxo)niobium (Nb (NCH₂CHMeCHMe₂)(O'Bu)₃), (3,3-dimethylbutylimido)tri(tert-butyloxo)niobium (Nb(NCH₂CH₂CMe₃)(O'Bu)₃), (1-ethylbutylimido)tri(tert-butyloxo)niobium (Nb(NCHEtPr)(O'Bu)₃), (2-ethylbutylimido)tri(tert-butyloxo)niobium (Nb(NCH₂CHEt₂)(O'Bu)₃), (1,1,2-trimethylpropylimido)tri(tert-butyloxo)niobium (Nb(NCMe₂CHMe₂)(O'Bu)₃), (1,2,2-trimethylpropylimido)tri(tert-butyloxo)niobium (Nb(NCHMeCMe₃)(O'Bu)₃), (1-ethyl-1-methylpropylimido)tri(tert-butyloxo)niobium (Nb(NCEt₂Me)(O'Bu)₃), (1-ethyl-2-methylpropylimido)tri(tert-butyloxo)niobium (Nb(NCHEtCHMe₂)(O'Bu)₃), (cyclobutylimido)tri(tert-butyloxo)niobium (Nb(N$^c$Bu)(O'Bu)₃), (cyclopentylimido)tri(tert-butyloxo)niobium (Nb(N$^c$Pe)(O'Bu)₃), (cyclohexylimido)tri(tert-butyloxo)niobium (Nb(N$^c$Hx)(O'Bu)₃), (cyclopropylmethylimido)tri(tert-butyloxo)niobium (Nb(NCH₂$^c$Pr)(O'Bu)₃), (cyclopropylethylimido)tri(tert-butyloxo)niobium (Nb(NCH₂CH₂$^c$Pr)(O'Bu)₃), (cyclobutylmethylimido)tri(tert-butyloxo)niobium (Nb(NCH₂$^x$Bu)(O'Bu)₃), (heptylimido)tri(tert-butyloxo)niobium (Nb(NHp)(O'Bu)₃), (cyclohexylmethylimido)tri(tert-butyloxo)niobium (Nb(NCH₂$^c$Hx)(O'Bu)₃), (1,1-diethyl-propylimido)tri(tert-butyloxo)niobium (Nb(NCEt₃)(O'Bu)₃), (2-methylcyclohexylimido)tri(tert-butyl oxo)niobium (Nb[N(2-MeC₆H₁₀)](O'Bu)₃), (4-methylcyclohexylimido)tri(tert-butyloxo)niobium (Nb[N(4-MeC₆H₁₀)](O'Bu)₃), (octylimido)tri(tert-butyloxo)niobium (Nb(NOct)(O'Bu)₃), (2,5-dimethylcyclohexylimido)tri(tert-butyloxo)niobium (Nb[N(2,5-Me₂C₆H₉)](O'Bu)₃), (3,5-dimethylcyclohexylimido)tri(tert-butyloxo)niobium (Nb[N(3,5-Me₂C₆H₉)](O'Bu)₃) and (1,1,3,3-tetramethylbutylimido)tri(tert-butyloxo)niobium (Nb(NCMe₂CH₂CMe₃)(O'Bu)₃) are preferred, and (tert-butylimido)tri(tert-butyloxo)niobium (Nb(N'Bu)(O'Bu)₃) is more preferred.

The reaction temperature in production method 6 of the present invention is not particularly limited and is appropriately selected from the range of preferably from 10 to 60° C., whereby the Group 5 metal oxo-alkoxo complex (3) of the present invention can be produced in a high yield.

In production method 6, the reaction time is not particularly limited and is appropriately selected from the range of preferably from 1 minute to 30 hours, more preferably from 10 minutes to 12 hours, whereby the Group 5 metal oxo-alkoxo complex (3) of the present invention can be produced in a high yield.

In production method 6, the molar ratio between the metal imido-trialkoxo complex (2a-Nb) and the benzaldehyde is not particularly limited, and the benzaldehyde is preferably reacted in an equimolar or greater amount, more preferably in an amount of 2 mol or more, per mol of metal imido-trialkoxo complex (2a-Nb), whereby the Group 5 metal oxo-alkoxo complex (3) of the present invention of the present invention can be produced in a high yield.

Production method 6 can be performed either in an organic solvent or under solvent-free conditions. From the standpoint that the yield of the Group 5 metal oxo-alkoxo complex (3) of the present invention is high, the production method 6 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (3) of the present invention, hexane, heptane, toluene and xylene are preferred. In the case of using an organic solvent in production method 6, the amount of the organic solvent used is not particularly limited, and the organic solvent is used in an appropriately selected amount, whereby the Group 5 metal oxo-alkoxo complex (3) of the present invention can be produced in a high yield.

The Group 5 metal oxo-alkoxo complex (3) of the present invention produced by production method 6 of the present invention may be purified, if desired, by appropriately using a general purification method such as filtration, extraction, distillation, sublimation, precipitation and crystallization.

Production method 7 is described below. Production method 7 of the present invention is a method of reacting a metal imido-trialkoxo complex (2a-Nb) with an aldehyde (7) to produce the Group 5 metal oxo-alkoxo complex (4) of the present invention.

Production Method 7:

[Chem. 14]

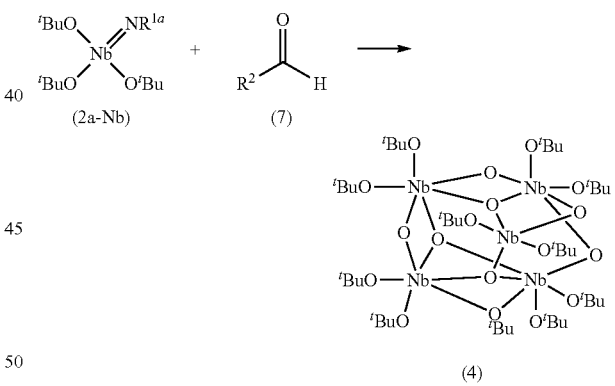

(wherein R² represents a phenyl group or a C₄-C₈ tertiary alkyl group; and R$^{1a}$ has the same meaning as above.)

As for the C₁-C₁₂ alkyl group represented by R$^{1a}$, from the standpoint that the yield of the Group 5 metal oxo-alkoxo complex (4) of the present invention is high, R$^{1a}$ is preferably a C₄-C₈ alkyl group, more preferably a tert-butyl group.

The definition of R² is described. Specific examples of the C₄-C₈ tertiary alkyl group represented by R² include a tert-butyl group, a tert-pentyl group, a 1,1-dimethylbutyl group, a 1-ethyl-1-methylpropyl group, a 1,1,2-trimethylpropyl group, a 1,1-dimethylpentyl group, a 1,1-diethylpropyl group, a 1-ethyl-1-methylbutyl group, a 1,1,2-trimethylbutyl group, a 1,1,3-trimethylbutyl group, a 1,1,2,2-tetramethylpropyl group, a 1,1-dimethylhexyl group, a 1,1-diethylbutyl group, a 1-methyl-1-propylbutyl group, a 1-ethyl-1-methylpentyl group, and a 1,1,3,3-tetramethylbutyl group. In view of high yield of the Group 5 metal oxo-alkoxo complex (3) or (4), $R^2$ is preferably a tert-butyl group, a tert-pentyl group or a phenyl group, more preferably a tert-butyl group or a phenyl group.

As for the metal imido-trialkoxo complex (2a-Nb) used as a raw material for synthesis in production method 7 of the present invention, from the standpoint that the yield of the Group 5 metal oxo-alkoxo complex (4) of the present invention is high, (butylimido)tri(tert-butyloxo)niobium (Nb(N$^t$Bu)(O$^t$Bu)$_3$), (isobutylimido)tri(tert-butyloxo)niobium (Nb(N$^s$Bu)(O$^t$Bu)$_3$), (tert-butylimido)tri(tert-butyloxo)niobium (Nb(N$^t$Bu)(O$^t$Bu)$_3$), (pentylimido)tri(tert-butyloxo)niobium (Nb(NPe)(OPe)$_3$), (isopentylimido)tri(tert-butyloxo)niobium (Nb(N$^i$Pe)(O$^t$Bu)$_3$), (neopentylimido)tri(tert-butyloxo)niobium (Nb(NNp)(O$^t$Bu)$_3$), (tert-pentylimido)tri(tert-butyloxo)niobium (Nb(N$^t$Pe)(O$^t$Bu)$_3$), (1-methylbutylimido)tri(tert-butyloxo)niobium (Nb(NCHMePr)(O$^t$Bu)$_3$), (2-methylbutylimido)tri(tert-butyloxo)niobium (Nb(NCH$_2$CHEtMe)(O$^t$Bu)$_3$), (1,2-dimethylpropylimido)tri(tert-butyloxo)niobium (Nb(NCHMeCHMe$_2$)(O$^t$Bu)$_3$), (hexylimido)tri(tert-butyloxo)niobium (Nb(NHx)(O$^t$Bu)$_3$), (isohexylimido)tri(tert-butyloxo)niobium (Nb(N$^i$Hx)(O$^t$Bu)$_3$), (1-methylpentylimido)tri(tert-butyloxo)niobium (Nb(NCHMeBu)(O$^t$Bu)$_3$), (2-methylpentyl imido)tri(tert-butyloxo)niobium (Nb(NCH$_2$CHMePr)(O$^t$Bu)$_3$), (3-methylpentylimido)tri(tert-butyloxo)niobium (Nb(NCH$_2$CH$_2$CHMeEt)(O$^t$Bu)$_3$), (1,1-dimethylbutylimido)tri(tert-butyl oxo)niobium (Nb(NCMe$_2$Pr)(O$^t$Bu)$_3$), (1,2-dimethylbutylimido)tri(tert-butyloxo)niobium (Nb(NCHMeCHMeEt)(O$^t$Bu)$_3$), (2,2-dimethylbutylimido)tri(tert-butyloxo)niobium (Nb(NCH$_2$CMe$_2$Et)(O$^t$Bu)$_3$), (1,3-dimethylbutylimido)tri(tert-butyloxo)niobium (Nb(NCHMeCH$_2$CHMe$_2$)(O$^t$Bu)$_3$), (2,3-dimethylbutylimido)tri(tert-butyl oxo)niobium (Nb(NCH$_2$CHMeCHMe$_2$)(O$^t$Bu)$_3$), (3,3-dimethylbutylimido)tri(tert-butyloxo)niobium (Nb(NCH$_2$CH$_2$CMe$_3$)(O$^t$Bu)$_3$), (1-ethylbutylimido)tri(tert-butyloxo)niobium (Nb(NCHEtPr)(O$^t$Bu)$_3$), (2-ethylbutylimido)tri(tert-butyloxo)niobium (Nb(NCH$_2$CHEt$_2$)(O$^t$Bu)$_3$), (1,1,2-trimethylpropylimido)tri(tert-butyloxo)niobium (Nb(NCMe$_2$CHMe$_2$)(O$^t$Bu)$_3$), (1,2,2-trimethylpropylimido)tri(tert-butyloxo)niobium (Nb(NCHMeCMe$_3$)(O$^t$Bu)$_3$), (1-ethyl-1-methylpropylimido)tri(tert-butyloxo)niobium (Nb(NCEt$_2$Me)(O$^t$Bu)$_3$), (1-ethyl-2-methylpropylimido)tri(tert-butyloxo)niobium (Nb(NCHEtCHMe$_2$)(O$^t$Bu)$_3$), (cyclobutylimido)tri(tert-butyloxo)niobium (Nb(N$^c$Bu)(O$^t$Bu)$_3$), (cyclopentylimido)tri(tert-butyloxo)niobium (Nb(N$^c$Pe)(O$^t$Bu)$_3$), (cyclohexylimido)tri(tert-butyloxo)niobium (Nb(N$^c$Hx)(O$^t$Bu)$_3$), (cyclopropylmethylimido)tri(tert-butyloxo)niobium (Nb(NCH$_2^c$Pr)(O$^t$Bu)$_3$), (cyclopropylethylimido)tri(tert-butyloxo)niobium (Nb(NCH$_2$CH$_2^c$Pr)(O$^t$Bu)$_3$), (cyclobutylmethylimido)tri(tert-butyloxo)niobium (Nb(NCH$_2^c$Bu)(O$^t$Bu)$_3$), (heptylimido)tri(tert-butyloxo)niobium (Nb(NHp)(O$^t$Bu)$_3$), (cyclohexylmethylimido)tri(tert-butyloxo)niobium (Nb(NCH$_2^c$Hx)(O$^t$Bu)$_3$), (1,1-diethylpropylimido)tri(tert-butyloxo)niobium (Nb(NCEt$_3$)(O$^t$Bu)$_3$), (2-methylcyclohexylimido)tri(tert-butyloxo)niobium (Nb[N(2-MeC$_6$H$_{10}$)](O$^t$Bu)$_3$), (4-methylcyclohexylimido)tri(tert-butyloxo)niobium (Nb[N(4-MeC$_6$H$_{10}$)](O$^t$Bu)$_3$), (octylimido)tri(tert-butyloxo)niobium (Nb(NOct)(O$^t$Bu)$_3$), (2,5-dimethylcyclohexylimido)tri(tert-butyl oxo)niobium (Nb[N(2,5-Me$_2$C$_6$H$_9$)](O$^t$Bu)$_3$), (3,5-dimethylcyclohexylimido)tri(tert-butyloxo)niobium (Nb[N(3,5-Me$_2$C$_6$H$_9$)](O$^t$Bu)$_3$) and (1,1,3,3-tetramethylbutylimido)tri(tert-butyloxo)niobium (Nb(NCMe$_2$CH$_2$CMe$_3$)(O$^t$Bu)$_3$) are preferred, and (tert-butylimido)tri(tert-butyloxo)niobium (Nb(N$^t$Bu)(O$^t$Bu)$_3$) is more preferred.

Specific examples of the aldehyde (7) used as a raw material for synthesis in production method 7 of the present invention include pivalaldehyde, 2,2-dimethylbutanal, 2,2-dimethylpentanal, 2-ethyl-2-methylbutanal, 2,2,3-trimethylbutanal, 1,1-dimethylhexanal, 1,1-diethylbutanal, 2-ethyl-2-methylpentanal, 2,2,3-trimethylpentanal, 2,2,4-trimethylpentanal, 2,2,3,3-tetramethylbutanal, 2,2-dimethylheptanal, 2,2-diethylpentanal, 2-methyl-2-propylpentanal, 2-methyl-2-ethylhexanal, 2,2,4,4-tetramethylpentanal, and benzaldehyde. From the standpoint that the yield of the Group 5 metal oxo-alkoxo complex (4) of the present invention is high, pivalaldehyde, 2,2-dimethylbutanal and benzaldehyde are preferred, and pivalaldehyde and benzaldehyde are more preferred.

The reaction temperature in production method 7 of the present invention is not particularly limited and is appropriately selected from the range of preferably from −80° C. to 60° C. when $R^2$ is a $C_4$-$C_8$ tertiary alkyl group, and from the range of preferably from −80° C. to 10° C. when $R^2$ is a phenyl group, whereby the Group 5 metal oxo-alkoxo complex (4) of the present invention can be produced in a high yield.

In production method 7, the reaction time is not particularly limited and is appropriately selected from the range of preferably from 1 minute to 30 hours, more preferably from 10 minutes to 12 hours, whereby the Group 5 metal oxo-alkoxo complex (4) of the present invention can be produced in a high yield.

In production method 7, as for the molar ratio between the metal imido-trialkoxo complex (2a-Nb) and the aldehyde (7), the metal imido-trialkoxo complex (2a-Nb) and the aldehyde (7) are preferably reacted in a molar ratio of 1:1.0 to 2.0, whereby the Group 5 metal oxo-alkoxo complex (4) of the present invention of the present invention can be produced in a high yield.

Production method 7 can be performed either in an organic solvent or under solvent-free conditions. From the standpoint that the yield of the Group 5 metal oxo-alkoxo complex (4) of the present invention is high, the production method 7 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (4) of the present invention, hexane, heptane, toluene and xylene are preferred. In the case of using an organic solvent in production method 7, the amount of the organic solvent used is not particularly limited, and the organic solvent is used in an appropriately selected amount, whereby the Group 5 metal oxo-alkoxo complex (4) of the present invention can be produced in a high yield.

The Group 5 metal oxo-alkoxo complex (4) of the present invention produced by production method 7 of the present invention may be purified, if desired, by appropriately using a general purification method such as filtration, extraction, distillation, sublimation, precipitation and crystallization.

Production method 8 of the present invention is described below. Production method 8 of the present invention is a method of reacting pentakis(tert-butyloxo)niobium (Nb(O$^t$Bu)$_5$) with diacetone alcohol in a molar ratio of less than 1.3 mol of diacetone alcohol per mol of pentakis(tert-butyloxo)niobium to produce the Group 5 metal oxo-alkoxo complex (4).

Production Method 8:

[Chem. 15]

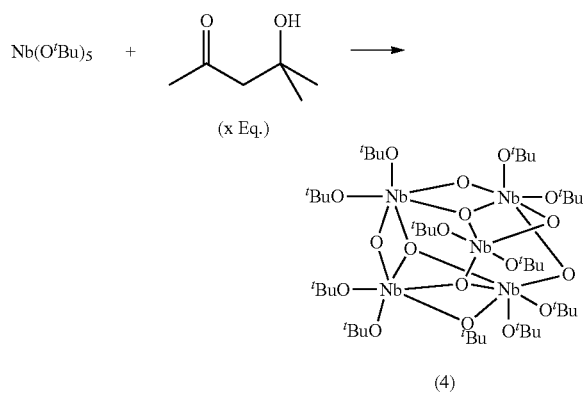

(wherein x represents a numerical value of less than 1.3.)

The pentakis(tert-butyloxo)niobium used as a raw material for synthesis in production method 8 of the present invention can be produced according to the above-described production method Nb1.

In production method 8 of the present invention, the molar ratio between the pentakis(tert-butyloxo)niobium and the diacetone alcohol is limited to less than 1.3 mol per mol of pentakis(tert-butyloxo)niobium, and in view of high yield of the Group 5 metal oxo-alkoxo complex (4) of the present invention, from 0.30 mol to less than 1.1 mol of diacetone alcohol is preferably reacted per mol of pentakis(tert-butyloxo)niobium.

The reaction temperature in production method 8 of the present invention is not particularly limited, and from the standpoint that the yield of the Group 5 metal oxo-alkoxo complex (4) of the present invention is high, the reaction temperature is preferably from −80° C. to 350° C., more preferably from −20° C. to 200° C., still more preferably from 0 to 60° C.

In production method 8, the reaction time is not particularly limited and is appropriately selected from the range of preferably from 1 minute to 10 days, more preferably from 1 to 24 hours, whereby the Group 5 metal oxo-alkoxo complex (4) of the present invention can be produced in a high yield.

Production method 8 can be performed either in an organic solvent or under solvent-free conditions. From the standpoint that the yield of the Group 5 metal oxo-alkoxo complex (4) of the present invention is high, the production method 8 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, mesitylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (4) of the present invention, hexane, heptane, toluene, xylene and mesitylene are preferred. In the case of using an organic solvent in production method 8, the amount of the organic solvent used is not particularly limited, and the organic solvent is used in an appropriately selected amount, whereby the Group 5 metal oxo-alkoxo complex (4) of the present invention can be produced in a high yield.

The Group 5 metal oxo-alkoxo complex (4) of the present invention produced by production method 8 may be purified, if desired, by appropriately using a general purification method such as filtration, extraction, distillation, sublimation, precipitation and crystallization.

The Group 5 metal oxo-alkoxo complex of the present invention represented by chemical formula (5) is described in detail.

Figure 6:
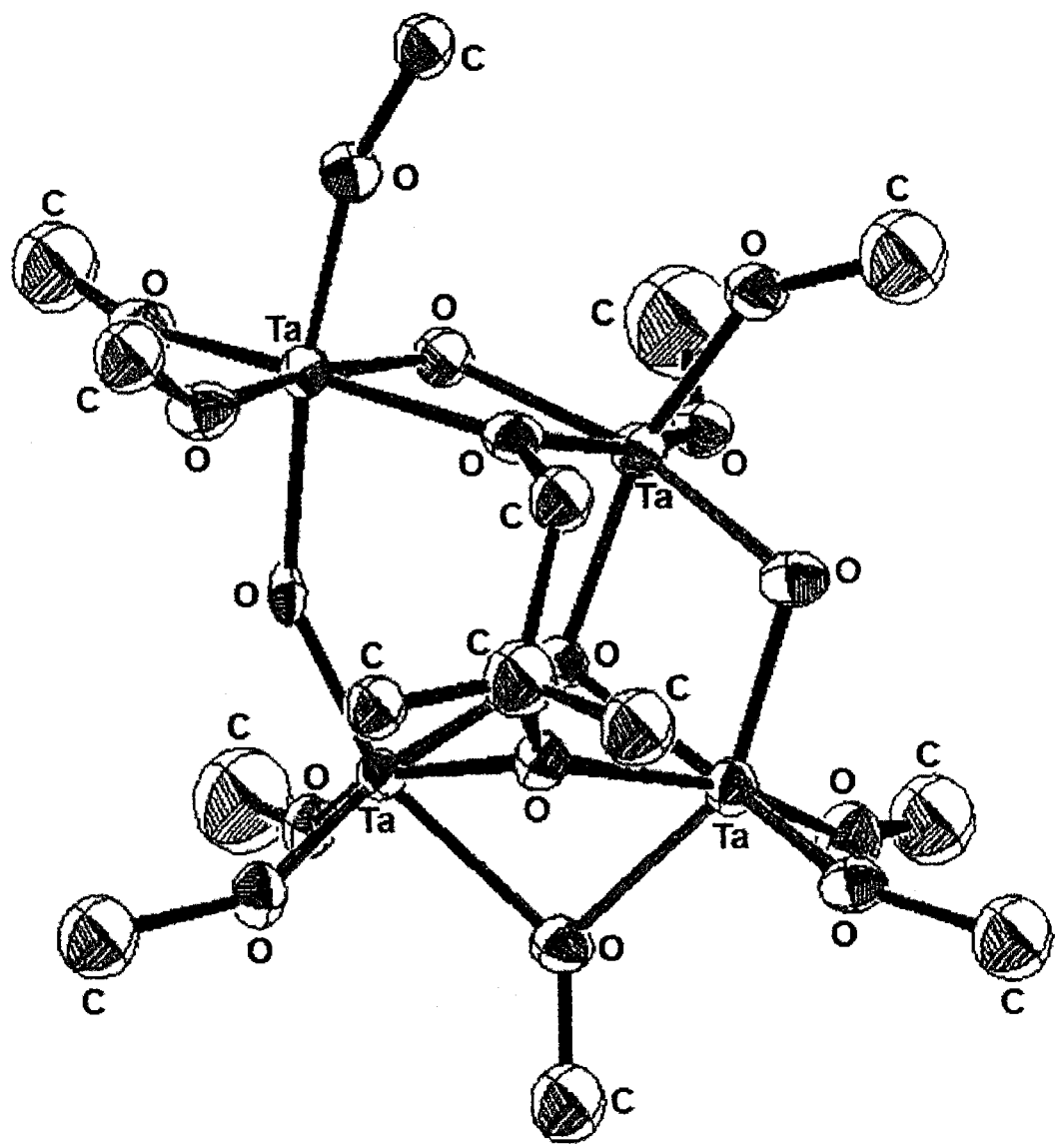
FIG. 6 is a view showing the molecular structure as the result of single-crystal X-ray structure analysis of the crystal obtained in Example 39; in the Figure, the depiction of the terminal methyl group of a tert-butyloxy group and all hydrogen atoms is omitted.

The Group 5 metal oxo-alkoxo complex of the present invention represented by chemical formula (5) has a molecular structure depicted in the later-described FIG. 6.

The production method of the Group 5 metal oxo-alkoxo complex (5) of the present invention represented by chemical formula (5) is described below. The Group 5 metal oxo-alkoxo complex (5) of the present invention can be produced according to the following production method 9. Production method 9 of the present invention is a method of reacting a metal imido-trialkoxo complex (2a-Ta) with one or more kinds of oxidants selected from the group consisting of oxygen, air and ozone to produce the Group 5 metal oxo-alkoxo complex (5) of the present invention.

Production Method 9:

[Chem. 16]

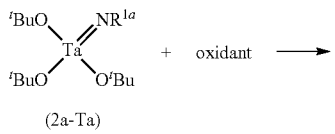

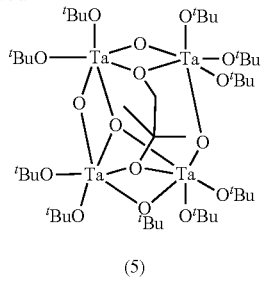

(5)

(wherein $R^{1a}$ has the same meaning as above.)

As for the $C_1$-$C_{12}$ alkyl group represented by $R^{1a}$, from the standpoint that the yield of the Group 5 metal oxo-alkoxo complex (5) of the present invention is high, $R^{1a}$ is preferably a $C_4$-$C_8$ alkyl group, more preferably a $C_4$-$C_5$ alkyl group, still more preferably a tert-butyl group.

The metal imido-trialkoxo complex (2a-Ta) used as a raw material for synthesis in production method 9 of the present invention can be produced according to the method described in JP-A-2008-266280.

As the metal imido-trialkoxo complex (2a-Ta), from the standpoint that the yield of the Group 5 metal oxo-alkoxo complex (5) of the present invention is high, (butylimido)tri(tert-butyloxo)tantalum (Ta(NBu)(O$^t$Bu)$_3$), (isobutylimido)tri(tert-butyloxo)tantalum (Ta(N$^i$Bu)(O$^t$Bu)$_3$), (sec-butylimido)tri(tert-butyloxo)tantalum (Ta(N$^s$Bu)(O$^t$Bu)$_3$), (tert-butylimido)tri(tert-butyloxo)tantalum (Ta(N$^t$Bu)(O$^t$Bu)$_3$), (pentylimido)tri(tert-butyloxo)tantalum (Ta(NPe)(O$^t$Bu)$_3$), (isopentylimido)tri(tert-butyloxo)tantalum (Ta(N$^i$Pe)(O$^t$Bu)$_3$), (neopentylimido)tri(tert-butyloxo)tantalum (Ta(NNp)(O$^t$Bu)$_3$), (tert-pentylimido)tri(tert-butyloxo)tantalum (Ta(N$^t$Pe)(O$^t$Bu)$_3$), (1-methylbutylimido)tri(tert-butyloxo)tantalum (Ta(NCHMePr)(O$^t$Bu)$_3$), (2-methylbutylimido)tri(tert-butyloxo)tantalum (Ta(NCH$_2$CHEtMe)(O$^t$Bu)$_3$), (1,2-dimethylpropylimido)tri(tert-butyloxo)tantalum (Ta(NCHMeCHMe$_2$)(O$^t$Bu)$_3$), (hexylimido)tri(tert-butyloxo)tantalum (Ta(NHx)(O$^t$Bu)$_3$), (isohexylimido)tri(tert-butyloxo)tantalum (Ta(N$^i$Hx)(O$^t$Bu)$_3$), (1-methylpentylimido)tri(tert-butyl oxo)tantalum (Ta(NCHMeBu)(O$^t$Bu)$_3$), (2-methylpentylimido)tri(tert-butyloxo)tantalum (Ta(NCH$_2$CHMePr)(O$^t$Bu)$_3$), (3-methylpentylimido)tri(tert-butyloxo)tantalum (Ta(NCH$_2$CH$_2$CHMeEt)(O$^t$Bu)$_3$), (1,1-dimethylbutylimido)tri(tert-butyloxo)tantalum (Ta(NCMe$_2$Pr)(O$^t$Bu)$_3$), (1,2-dimethylbutylimido)tri(tert-butyloxo)tantalum (Ta(NCHMeCHMeEt)(O$^t$Bu)$_3$), (2,2-dimethylbutylimido)tri(tert-butyloxo)tantalum (Ta(NCH$_2$CMe$_2$Et)(O$^t$Bu)$_3$), (1,3-dimethylbutylimido)tri(tert-butyloxo)tantalum (Ta(NCHMeCH$_2$CHMe$_2$)(O$^t$Bu)$_3$), (2,3-dimethylbutylimido)tri(tert-butyloxo)tantalum (Ta(NCH$_2$CHMeCHMe$_2$)(O$^t$Bu)$_3$), (3,3-dimethylbutylimido)tri(tert-butyloxo)tantalum (Ta(NCH$_2$CH$_2$CMe$_3$)(O$^t$Bu)$_3$), (1-ethylbutylimido)tri(tert-butyloxo)tantalum (Ta(NCHEtPr)(O$^t$Bu)$_3$), (2-ethylbutylimido)tri(tert-butyloxo)tantalum (Ta(NCH$_2$CHEt$_2$)(O$^t$Bu)$_3$), (1,1,2-trimethylpropylimido)tri(tert-butyloxo)tantalum (Ta(NCMe$_2$CHMe$_2$)(O$^t$Bu)$_3$), (1,2,2-trimethylpropylimido)tri(tert-butyloxo)tantalum (Ta(NCHMeCMe$_3$)(O$^t$Bu)$_3$), (1-ethyl-1-methylpropylimido)tri(tert-butyloxo)tantalum (Ta(NCEt$_2$Me)(O$^t$Bu)$_3$), (1-ethyl-2-methylpropylimido)tri(tert-butyloxo)tantalum (Ta(NCHEtCHMe$_2$)(O$^t$Bu)$_3$), (cyclobutylimido)tri(tert-butyloxo)tantalum (Ta(N$^c$Bu)(O$^t$Bu)$_3$), (cyclopentylimido)tri(tert-butyloxo)tantalum (Ta(N$^c$Pe)(O$^t$Bu)$_3$), (cyclohexylimido)tri(tert-butyloxo)tantalum (Ta(N$^c$Hx)(O$^t$Bu)$_3$), (cyclopropylmethylimido)tri(tert-butyloxo)tantalum (Ta(NCH$_2^c$Pr)(O$^t$Bu)$_3$), (cyclopropylethylimido)tri(tert-butyloxo)tantalum (Ta(NCH$_2$CH$_2^c$Pr)(O$^t$Bu)$_3$), (cyclobutylmethylimido)tri(tert-butyloxo)tantalum (Ta(NCH$_2^c$Bu)(O$^t$Bu)$_3$), (heptylimido)tri(tert-butyloxo)tantalum (Ta(NHp)(O$^t$Bu)$_3$), (cyclohexylmethylimido)tri(tert-butyloxo)tantalum (Ta(NCH$_2^c$Hx)(O$^t$Bu)$_3$), (1,1-diethyl-propylimido)tri(tert-butyloxo)tantalum (Ta(NCEt$_3$)(O$^t$Bu)$_3$), (2-methylcyclohexylimido)tri(tert-butyloxo)tantalum (Ta(2-MeC$_6$H$_{10}$)](O$^t$Bu)$_3$), (4-methylcyclohexylimido)tri(tert-butyloxo)tantalum (Ta(4-MeC$_6$H$_{10}$)](O$^t$Bu)$_3$), (octylimido)tri(tert-butyloxo)tantalum (Ta(NOct)(O$^t$Bu)$_3$), (2,5-dimethylcyclohexylimido)tri(tert-butyloxo)tantalum (Ta[N(2,5-Me$_2$C$_6$H$_9$)](O$^t$Bu))$_3$), (3,5-dimethylcyclohexylimido)tri(tert-butyloxo)tantalum (Ta[N(3,5-Me$_2$C$_6$H$_9$)](O$^t$Bu)$_3$) and (1,1,3,3-tetramethylbutylimido)tri(tert-butyloxo)tantalum (Ta(NCMe$_2$CH$_2$CMe$_3$)(O$^t$Bu)$_3$) are preferred; Ta(NBu)(O$^t$Bu)$_3$, Ta(N$^i$Bu)(O$^t$Bu)$_3$, Ta(N$^s$Bu)(O$^t$Bu)$_3$, Ta(N$^t$Bu)(O$^t$Bu)$_3$, Ta(NPe)(O$^t$Bu)$_3$, Ta(N$^i$Pe)(O$^t$Bu)$_3$, (Ta(NNp)(O$^t$Bu)$_3$, Ta(N$^t$Pe)(O$^t$Bu)$_3$, Ta(NCHMePr)(O$^t$Bu)$_3$, Ta(NCH$_2$CHEtMe)(O$^t$Bu)$_3$ and Ta(NCHMeCHMe$_2$)(O$^t$Bu)$_3$ are more preferred; and Ta(N$^t$Bu)(O$^t$Bu)$_3$ is still more preferred.

The kind of the oxidant is described below. Oxidants that can be used in production method 9 of the present invention are oxygen, air and ozone. Of these oxidants, one kind may be used alone, or two or more kinds may be mixed in an arbitrary ratio and used. From the standpoint that the yield of the Group 5 metal oxo-alkoxo complex (5) of the present invention is high, oxygen and air are preferably used, and oxygen is more preferred.

As to the molar ratio between the metal imido-trialkoxo complex (2a-Ta) and the oxidant in production method 9 of the present invention, in view of high yield, an equimolar or greater amount of oxidant is preferably reacted per mol of metal imido-trialkoxo complex (2a-Ta). In the case where the oxidant is oxygen or air, it is more preferable to react the oxidant in an amount of 5 times by mol or more per mol of metal imido-trialkoxo complex (2a-Ta). The oxidant may be diluted, if desired, with an inert gas such as helium, neon, argon, krypton, xenon and nitrogen. From the standpoint that production method 9 of the present invention can be safely performed, the oxidant is preferably used by diluting it with an inert gas. In the case of using the oxidant by diluting it, the mixing ratio between the oxidant and the inert gas is not particularly limited, and these may be mixed in an arbitrary ratio.

Production method 9 can be performed either in an organic solvent or under solvent-free conditions. From the standpoint that the yield of the Group 5 metal oxo-alkoxo complex (5) of the present invention is high, the production method 9 is preferably performed in an organic solvent. The organic solvent that can be used is not limited as long as it is an organic solvent not inhibiting the reaction. Examples of the organic solvent that can be used include an aliphatic hydrocarbon such as pentane, hexane, cyclohexane, heptane, methylcyclohexane, ethylcyclohexane and octane, an aromatic hydrocarbon such as benzene, toluene, ethylbenzene, xylene, trifluoromethylbenzene and benzotrifluoride, an ether such as diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane and tetrahydrofuran, a haloalkane such as dichloromethane, chloroform, 1,1-dichloroethane, 1,2-dichloroethane, 1,1,1-trichloroethane and 1,1,2-trichloroethane, a carboxylic acid amide such as N,N-dimethylformamide and N,N-dimethylacetamide, and a sulfoxide such as dimethyl sulfoxide and diethyl sulfoxide. Of these organic solvents, one kind may be used alone, or two or more kinds may be mixed in an arbitrary ratio and used. In view of high yield of the Group 5 metal oxo-alkoxo complex (5) of the present invention, hexane, heptane, toluene and xylene are preferred. In the case of using an organic solvent in production method 9, the amount of the organic solvent used is not particularly limited, and the organic solvent is used in an appropriately selected amount, whereby the Group 5 metal oxo-alkoxo complex (5) of the present invention can be produced in a high yield.

The reaction temperature in production method 9 of the present invention is limited to less than 60° C., and from the standpoint that the yield of the Group 5 metal oxo-alkoxo complex (5) of the present invention is high, the reaction temperature is preferably from −20° C. to less than 60° C., more preferably from 0 to less than 40° C.

The reaction time is not particularly limited and is appropriately selected from the range of preferably from 1 to 30 days, more preferably from 3 to 20 day, whereby the Group 5 metal oxo-alkoxo complex (5) of the present invention can be produced in a high yield.

The Group 5 metal oxo-alkoxo complex (5) of the present invention produced by production method 9 of the present invention may be purified, if desired, by appropriately using a general purification method such as filtration, extraction, distillation, sublimation, precipitation and crystallization.

The film-forming material of the present invention is described below.

The film-forming material of the present invention is characterized by containing a Group 5 metal oxo-alkoxo complex represented by formula (A) and an organic solvent in a weight ratio of from 1:0.1 to 1:1,000,000.

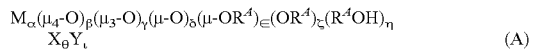

(A)

(wherein M represents a niobium atom or a tantalum atom; $R^A$ represents a $C_1$-$C_6$ alkyl group; X represents a $C_1$-$C_8$ alkylenedioxy group that may be substituted with a phenyl group; Y represents a $C_2$-$C_8$ carboxy group that may be substituted with a halogen atom, or an acetylacetonate group; α represents an integer of 3 to 10; β represents 0 or 1; γ represents an integer of 0 to 8; δ represents an integer of 2 to 9; ∈ represents an integer of 0 to 6; ζ represents an integer of 6 to 16; η represents an integer of 0 to 4; θ represents an integer of 0 to 2; and ι represents an integer of 0 to 6, provided that α to ι represent integers satisfying 5α=2(β+γ+δ+θ)+∈+ζ+ι).

Definitions of $R^A$, X and Y are described. The $C_1$-$C_6$ alkyl group represented by $R^A$ may be any of a linear alkyl group, a branched alkyl group, and a cyclic alkyl group. Specific examples thereof include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, a cyclopropyl group, a cyclobutyl group, a cyclopentyl group, a cyclohexyl group, a cyclopropylmethyl group, a cyclopropylethyl group, and a cyclobutylmethyl group. From the standpoint that the storage stability of the Group 5 metal oxo-alkoxo complex represented by formula (A) of the present invention is good, $R^A$ is preferably an ethyl group, an isopropyl group, a tert-butyl group or a neopentyl group, more preferably a tert-butyl group.

Specific examples of the $C_1$-$C_8$ alkylenedioxy group represented by X, which may be substituted with a phenyl group, include a μ$_4$-benzylidenedioxy group, a μ$_4$-2-methyl-1,2-propanedioxy group, and a μ-2,3-dimethyl-2,3-butanedioxy group.

Specific examples of the $C_2$-$C_8$ carboxy group represented by Y, which may be substituted with a halogen atom, include a μ-trichloroacetyloxy group, a μ-trifluoroacetyloxy group, a μ-acetyloxy group, a μ-2,2-dimethylbutanecarboxy group, a μ-2,2,2-trimethylacetyloxy group, a μ-3,3-dimethylbutanecarboxy group, and a μ-2-methyl-2-propenecarboxy group.

Specific examples of the Group 5 metal oxo-alkoxo complex represented by formula (A) include hexadekakis(tert-butyloxo)(μ$_4$-oxo)octakis(μ$_3$-oxo)octakis(μ-oxo)decaniobium (Nb$_{10}$(μ$_4$-O)(μ$_3$-O)$_8$(μ-O)$_8$(O$^t$Bu)$_{16}$), hexadekakis(tert-butyloxo)(μ$_4$-oxo)octakis(μ$_3$-oxo)octakis(μ-oxo)decatantalum (Ta$_{10}$(μ$_4$-O)(μ$_3$-O)$_8$(μ-O)$_8$(O$^t$Bu)$_{16}$), (μ-tert-butyloxo)tetradecakis(tert-butyloxo)(μ$_4$-oxo)pentakis(μ$_3$-oxo)nonakis(μ-oxo)nonaniobium (Nb$_9$(μ$_4$-O)(μ$_3$-O)$_5$(μ-O)$_9$(μ-O$^t$Bu)(O$^t$Bu)$_{14}$), (1-tert-butyloxo)tetradecakis(tert-butyloxo)(μ$_4$-oxo)pentakis(μ$_3$-oxo)nonakis(μ-oxo)nonatantalum (Ta$_9$(μ$_4$-O)(μ$_3$-O)$_5$(μ-O)$_9$(μ-O$^t$Bu)(O$^t$Bu)$_{14}$), (μ-tert-butyloxo)nonakis(tert-butyloxo)(μ$_3$-oxo)tris(μ-oxo)(μ$_4$-benzylidenedioxo)tetraniobium (Nb$_4$(μ$_4$-O$_2$CHPh)(μ$_3$-O)(μ-O)$_3$(μ-O$^t$Bu)(O$^t$Bu)$_9$), (μ-tert-butyloxo)decakis(tert-butyloxo)tris(μ$_3$-oxo)tetrakis(μ-oxo)pentaniobium (Nb$_5$(μ$_3$-O)$_3$(μ-O)$_4$(μ-O$^t$Bu)(O$^t$Bu)$_{10}$), (μ-tert-butyloxo)nonakis(tert-butyloxo)(μ$_3$-oxo)tris(μ-oxo)(μ$_4$-2-methyl-1,2-propanedioxo)tetratantalum (Ta$_4$(μ$_4$-OCMe$_2$CH$_2$O)(μ$_3$-O)(μ-O)$_3$(μ-O$^t$Bu)(O$^t$Bu)$_9$), hexakis(μ-ethyloxo)tetradecakis(ethyloxo)bis(μ$_3$-oxo)octakis(μ-oxo)octaniobium (Nb$_8$(μ$_3$-O)$_2$(μ-O)$_8$(μ$_3$-OEt)$_6$(OEt)$_{14}$), bis(μ-isopropyloxo)dodecakis(isopropyloxo)bis(isopropyl alcohol)bis(μ$_3$-oxo)hexakis(μ-oxo)hexaniobium (Nb$_6$(μ$_3$-O)$_2$(μ-O)$_6$(μ-O$^i$Pr)$^2$(O$^i$Pr)$_{12}$($^i$PrOH)$_2$), hexakis(μ-trichloroacetyloxo)hexakis(μ-ethyloxo)hexakis(ethyloxo)tris(μ-oxo)hexaniobium (Nb$_6$(μ-O)$_3$(μ-OEt)$_6$(OEt)$_6$(μ-O$_2$CCl$_3$)$_6$), hexakis(μ-trifluoroacetyloxo)hexakis(μ-ethyloxo)hexakis(ethyloxo)tris(μ-oxo)hexaniobium (Nb$_6$(μ-O)$_3$(μ-OEt)$_6$(OEt)$_6$(μ-O$_2$CCF$_3$)$_6$), octakis(isopropyloxo)tetrakis(μ-oxo)tetrakis(μ-acetyloxo)tetraniobium (Nb$_4$(μ-O)$_4$(O$^i$Pr)$_8$(μ-O$_2$CMe)$_4$), octakis(ethyloxo)tetrakis(μ-oxo)tetrakis(acetylacetonato)tetraniobium (Nb$_4$(μ-O)$_4$(OEt)$_8$(acac)$_4$), octakis(isopropyloxo)bis(μ$_3$-oxo)bis(μ-oxo)bis(μ-2,3-dimethyl-2,3-butanedioxo)tetraniobium (Nb$_4$(μ$_3$-O)$_2$(μ-O)$_2$(O$^i$Pr)$_8$(μ-OCMe$_2$CMe$_2$O)$_2$), octakis(neopentyloxo)tetrakis(μ-oxo)tetrakis(μ-2,2-dimethylbutanecarboxy)tetraniobium (Nb$_4$(μ-O)$_4$(ONp)$_8$(μ-O$_2$CNp)$_4$), tetrakis(μ-isopropyloxo)tridecakis(isopropyloxo)tris(μ$_3$-oxo)hexakis(μ-oxo)heptatantalum (Ta$_7$(μ$_3$-O)$_3$(μ-O)$_6$(μ-O$^i$Pr)$_4$(O$^i$Pr)$_{13}$), (μ-tert-butyloxo)decakis(tert-butyloxo)tetrakis(μ-oxo)tris(μ-oxo)pentatantalum (Ta$_5$(μ$_3$-O)$_4$(μ-O)$_3$(μ-O$^t$Bu)(O$^t$Bu)$_{10}$), hexakis(μ-ethyloxo)tetradecakis(ethyloxo)bis(μ$_3$-oxo)octakis(μ-oxo)octatantalum (Ta$_8$(μ$_3$-O)$_2$(μ-O)$_8$(μ-OEt)$_6$(OEt)$_{14}$), octakis(neopentyloxo)tetrakis(μ-oxo)tetrakis(μ-2,2,2-trimethylacetyloxo)tetratantalum (Ta$_4$(μ-O)$_4$(ONp)$_8$(μ-O$_2$C$^t$Bu)$_4$), octakis(neopentyloxo)tetrakis(μ-oxo)tetrakis(μ-3,3-dimethylbutanecarboxy)tetratantalum (Ta$_4$(μ-O)$_4$(ONp)$_8$(μ-

O$_2$CNp)$_4$), and octakis(ethyloxo)tetrakis(μ-oxo)tetrakis(μ-2-methyl-2-propenecarboxy)tetratantalum (Ta$_4$(μ-O)$_4$(OEt)$_8$[μ-O$_2$CC(CH$_2$)CH$_3$]$_4$). Out of the Group 5 metal oxo-alkoxo complex represented by formula (A), a Group 5 metal oxo-alkoxo complex represented by formula (1), chemical formula (3), chemical formula (4) or chemical formula (5) is preferred.

From the standpoint that the thickness of the Group 5 metal oxide film is easy to control, the weight ratio between the Group 5 metal oxo-alkoxo complex of the present invention represented by formula (A) and the organic solvent is preferably from 1:1.5 to 1:1,000. Examples of the organic solvent that can be used include an alcohol, an aliphatic hydrocarbon, an aromatic hydrocarbon, an ether, a ketone, a carboxylic acid, and an ester.

Examples of the alcohol that can be used include a monool such as methanol, ethanol, propanol, isopropyl alcohol, butanol, sec-butyl alcohol, isobutyl alcohol, tert-butyl alcohol, tert-pentyl alcohol, cyclopentyl alcohol, hexanol, cyclohexyl alcohol and octanol, a cellosolve such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, diethylene glycol monopropyl ether, diethylene glycol monobutyl ether, propylene glycol monomethyl ether, propylene glycol monoethyl ether, propylene glycol monopropyl ether, propylene glycol monobutyl ether, 2-dimethylaminoethanol and 2-diethylaminoethanol, a diol such as ethylene glycol, 1,3-propanediol, 1,2-butanediol, 1,3-butanediol, 1,4-butanediol, 2,3-butanediol, 1,5-pentanediol, 1,2-hexanediol, 1,5-hexanediol, 1,6-hexanediol, 2,5-hexanediol, pinacol, 1,7-heptanediol, 1,2-octanediol, 1,8-octanediol, 1,3-nonanediol, 1,9-nonanediol, 1,2-decanediol, 1,10-decanediol, 2,7-dimethyl-3,6-octanediol, 2,2-dibutyl-1,3-propanediol, 1,2-dodecanediol, 1,12-dodecanediol, 1,2-tetradecanediol, 1,14-tetradecanediol, 2,2,4-trimethyl-1,3-pentane diol, 2,4-pentanediol, 1,2-cyclohexanedimethanol, 1,3-cyclohexanedimethanol, 1-hydroxymethyl-2-(2-hydroxyethyl)cyclohexane, 1-hydroxy-2-(3-hydroxypropyl)cyclohexane, 1-hydroxy-2-(2-hydroxyethyl)cyclohexane, 1-hydroxymethyl-2-(2-hydroxyethyl)benzene, 1-hydroxymethyl-2-(3-hydroxypropyl)benzene, 1-hydroxy-2-(2-hydroxyethyl)benzene, 1,2-benzyldimethylol, 1,3-benzyldimethylol, 1,2-cyclohexanediol, 1,3-cyclohexanediol, 1,4-cyclohexanediol and catechol, a triol such as glycerin, 1,2,6-hexanetriol and 3-methyl-1,3,5-pentanetriol, and a tetraol such as 1,3,5,7-cyclooctanetetraol.

Examples of the aliphatic hydrocarbon that can be used include pentane, hexane, heptane, octane, nonane, cyclohexane, methylcyclohexane, and ethylcyclohexane.

Examples of the aromatic hydrocarbon that can be used include benzene, toluene, ethylbenzene, and xylene.

Examples of the ether that can be used include diethyl ether, diisopropyl ether, dibutyl ether, cyclopentyl methyl ether, cyclopentyl ethyl ether, ethylene glycol dimethyl ether, ethylene glycol diethyl ether, diethylene glycol dimethyl ether, 1,3-propanediol dimethyl ether, 1,2-butanediol dimethyl ether, 1,3-butanediol dimethyl ether, 1,4-butanediol dimethyl ether, 2,3-butanediol dimethyl ether, 1,4-dioxane, 1,3-dioxane, tetrahydrofuran, 2-methoxyethyl acetate, and 3-methoxypropyl acetate.

Examples of the ketone that can be used include acetone, methyl ethyl ketone, diethyl ketone, isopropyl methyl ketone, tert-butyl methyl ketone, acetylacetone, diacetyl, and cyclohexanone.

Examples of the carboxylic acid that can be used include formic acid, acetic acid, propionic acid, butyric acid, malonic acid, and oxalic acid.

Examples of the ester that can be used include a formic acid ester such as methyl formate, ethyl formate, propyl formate and isopropyl formate, an acetic acid ester such as methyl acetate, ethyl acetate, propyl acetate and isopropyl acetate, and a cyclic ester such as γ-butyrolactone.

From the standpoint that a good Group 5 metal oxide film can be manufactured, the organic solvent is preferably an aliphatic hydrocarbon or an aromatic hydrocarbon, more preferably an aromatic hydrocarbon, still more preferably benzene, toluene or xylene.

Of these organic solvents, any two or more kinds may be mixed in an arbitrary ratio and used.

The film-forming material of the present invention may contain, if desired, a leveling agent, a defoaming agent, a thickener, a rheology modifier, etc.

Examples of the leveling agent include a fluorine-containing surfactant, silicone, an organic modified polysiloxane, acrylic resin, methyl acrylate, methyl methacrylate, ethyl acrylate, ethyl methacrylate, propyl acrylate, propyl methacrylate, isopropyl acrylate, isopropyl methacrylate, butyl acrylate, butyl methacrylate, sec-butyl acrylate, sec-butyl methacrylate, isobutyl acrylate, isobutyl methacrylate, tert-butyl acrylate, tert-butyl methacrylate, allyl acrylate, allyl methacrylate, benzyl acrylate, benzyl methacrylate, cyclohexyl acrylate, and cyclohexyl methacrylate.

Examples of the defoaming agent include silicone, a surfactant, a polyether, a higher alcohol, a glycerin higher fatty acid ester, a glycerin acetic acid higher fatty acid ester, a glycerin lactic acid higher fatty acid ester, a glycerin citric acid higher fatty acid ester, a glycerin succinic acid higher fatty acid ester, a glycerin diacetyl tartaric acid higher fatty acid ester, a glycerin acetic acid ester, a polyglycerin higher fatty acid ester, and a polyglycerin condensed ricinoleate.

Examples of the thickener include polyvinyl alcohol, acrylic resin, polyethylene glycol, polyurethane, hydrogenated castor oil, aluminum stearate, zinc stearate, aluminum octylate, fatty acid amide, polyethylene oxide, a dextrin fatty acid ester, dibenzylidene sorbitol, vegetable oil-type polymerized oil, surface-treated calcium carbonate, organic bentonite, silica, hydroxyethyl cellulose, methyl cellulose, carboxymethyl cellulose, sodium alginate, casein, sodium caseinate, xanthane gum, urethane-modified polyether, poly(acrylic acid-acrylic acid ester), and montmorillonite.

Examples of the rheology modifier include oxidized polyolefin amide, a fatty acid amide type, an oxidized polyolefin type, urea-modified urethane, methylene diisocyanate, trimethylene diisocyanate, tetramethylene diisocyanate, hexamethylene diisocyanate, ω,ω'-dipropyl ether diisocyanate, thiodipropyl diisocyanate, cyclohexyl-1,4-diisocyanate, dicyclohexylmethane-4,4'-diisocyanate, 1,5-dimethyl-2,4-bis(isocyanatomethyl)benzene, 1,5-dimethyl-2,4-bis(o)-isocyanatoethyl)benzene, 1,3,5-trimethyl-2,4-bis(isocyanatomethyl)benzene, and 1,3,5-triethyl-2,4-bis(isocyanatomethyl)benzene.

A composite oxide film may also be manufactured by using the film-forming material of the present invention together with other film-forming materials. Examples of the composite oxide include a niobic acid-based composite oxide such as lithium niobate, sodium niobate, potassium niobate, barium niobate, strontium niobate, strontium barium niobate, a tantalum-based composite oxide such as lithium tantalate, sodium tantalate, potassium tantalate, barium tantalate, strontium tantalate and strontium barium tantalate, a niobium- or tantalum-doped titania or zirconia, and a doped oxide of strontium titanate.

The method for manufacturing a Group 5 metal oxide film by using the film-forming material of the present invention (hereinafter, referred to as the manufacturing method of the present invention) is described below. The manufacturing method of the present invention is a method of applying the film-forming material of the present invention on a surface of a substrate and heat-treating the substrate to produce a Group 5 metal oxide film.

Examples of the method for applying the film-forming material on a surface of a substrate include a general method employed by one skilled in the art in the process of manufacturing a film by a wet process. Specific examples thereof include a spin coating method, a dip coating method, a spray coating method, a flow coating method, a roll coating method, a curtain coating method, a bar coating method, an ultrasonic coating method, a screen printing method, brush coating, and sponge coating. From the standpoint that the cost benefit is high and a good Group 5 metal oxide film can be manufactured, a spin coating method, a dip coating method, a spray coating method and a bar coating method are preferred.

The kind of the substrate that can be used in the manufacturing method of the present invention is not particularly limited, and, for example, a resin substrate such as polyimide resin, polyethylene terephthalate resin, polyethylene resin, polypropylene resin, polycarbonate resin, acrylic resin, polyester resin, ABS resin, AAS resin, polyvinyl chloride resin and polyethylene naphthalate, and a composite resin substrate obtained by compounding these resins may be used. In addition, an inorganic substrate, for example, glass, quartz, ceramics such as porcelain, silicon, various metals, various metal oxide films, and a composite material thereof, may be used. It is also possible to use a composite substrate in which a resin substrate and an inorganic substrate are combined.

The heat treatment temperature in the manufacturing method of the present invention is not particularly limited and is preferably not more than the thermal deformation temperature of the substrate used. In addition, by using the manufacturing method of the present invention, a Group 5 metal oxide film can be manufactured even through heat treatment at a low temperature. The temperature is specifically in the range of preferably from 20 to 1,000° C., more preferably from 20 to 700° C., still more preferably from 20 to 400° C., yet still more preferably from 20 to 200° C.

The heat treatment time is not particularly limited and for the reason that a necessary and sufficient heat treatment can be applied, the treatment time is preferably from 1 minute to 5 hours, more preferably from 1 to 30 minutes.

According to the manufacturing method of the present invention, not only a single-layer film but also a multilayer film consisting of two or more layers can be manufactured. For manufacturing a multilayer film, both a sequential lamination method where a method of applying one layer and applying a heat treatment is repeated, and a lamination method where after forming multiple layers by repeating the coating, the layers are en bloc heat-treated, can be employed.

The Group 5 metal oxide film manufactured using the group 5 metal oxo-alkoxo complex represented by formula (A) of the present invention can be used, for example, as a transparent electroconductive film of a solar cell, etc., a high-dielectric-constant film of a semiconductor device, etc., an insulating film, an antireflection film of a touch panel, etc., a hardcoat material, a scratch repairing material for glass, etc., a gas barrier material, and a photocatalytic member. Specific examples of the industrial product for which the film is used include electric appliances such as television, radio, computer and cellular phone, interior and exterior materials for building, interior and exterior materials for vehicle, ship, aircraft, etc., various glasses such glass fiber, glass powder and glass sheet, window members for vehicle, ship, aircraft, etc., mirrors, lighting devices, tiles, medical devices, medical instruments, medical materials, hygienic articles, film-forming devices for the production of semiconductor, etc., plasma treatment devices (plasma etching device, plasma cleaning device, ashing device), optical cells, and microfluidic chips.

EXAMPLES

The present invention is described in greater detail below by referring to Examples, but the present invention is not limited thereto. Unless otherwise indicated, all reaction operations were performed in an argon atmosphere.

Reference Example-1

[Chem. 17]

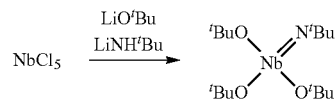

4.58 g of tert-butyl alcohol and 3.02 g of tert-butylamine were added to 62.4 mL of a hexane solution (1.65 M) of butyllithium and stirred at room temperature for 11 hours. The resulting solution was added to a hexane (20 mL) suspension containing 5.56 g (20.6 mmol) of niobium pentachloride and the mixture was stirred at room temperature for 24 hours. Insoluble matters were filtered, and the solvent was removed from the filtrate by distillation under reduced pressure. The residue was distilled under reduced pressure to obtain (tert-butylimido)tri(tert-butyloxo)niobium (Nb(N$^t$Bu)(O$^t$Bu)$_3$) as a colorless liquid. Yield quantity: 6.04 g (yield: 77%).

$^1$H NMR (500 MHz, C$_6$D$_6$) δ 1.38 (s, 27H), 1.37 (s, 9H).
$^{13}$C NMR (125 MHz, C$_6$D$_6$) δ 77.5 (br), 66.2 (br), 33.8, 32.9.

Reference Example-2

[Chem. 18]

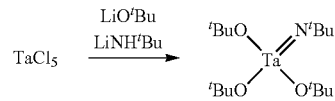

2.70 g of tert-butyl alcohol and 1.77 g of tert-butylamine were added to 36.7 mL of a hexane solution (1.65 M) of butyllithium and the mixture was stirred at room temperature for 12 hours. The resulting solution was added to a hexane (10 mL) suspension containing 4.34 g (12.1 mmol) of tantalum pentachloride and stirred at room temperature for 8 hours. Insoluble matters were filtered, and the solvent was removed from the filtrate by distillation under reduced pressure. The residue was distilled under reduced pressure to obtain (tert-butylimido)tri(tert-butyloxo)tantalum (Ta(N$^t$Bu)(O$^t$Bu)$_3$) as a colorless liquid. Yield quantity: 4.48 g (yield: 78%).

$^1$H NMR (500 MHz, C$_6$D$_6$) δ 1.43 (s, 9H), 1.38 (s, 27H).
$^{13}$C NMR (125 MHz, C$_6$D$_6$) δ 77.9, 64.4, 35.3, 33.0.

Example-1

[Chem. 19]

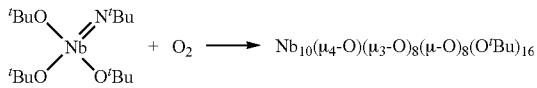

A solution prepared by mixing 2.03 g (5.30 mmol) of (tert-butylimido)tri(tert-butyloxo)niobium (Nb(N$^t$Bu)(O$^t$Bu)$_3$) and 7.5 mL of toluene was put in a reaction vessel and freeze-deaerated, and an oxygen-argon mixed gas (oxygen:argon=20 mol %:80 mol %) filling a balloon having an inner volume of 5 liter was introduced into the reaction vessel. After refluxing the solution for 379 hours, volatile components were removed from the reaction solution under reduced pressure, and soluble components were extracted by adding 10 mL of toluene to the remaining solid. Subsequently, 40 mL of acetonitrile was added to the extraction liquid to precipitate a crude product, and the crude product was washed with 5 mL of acetonitrile three times. The crude product was again dissolved in 2 mL of toluene to form a uniform solution, and 40 mL of acetonitrile was added thereto to precipitate a white solid. The white solid was washed with 5 mL of acetonitrile three times and then dried under reduced pressure to obtain hexadecakis(tert-butyloxo)(μ$_4$-oxo)octakis(μ$_3$-oxo)octakis(μ-oxo)decaniobium (Nb$_{10}$(μ$_4$-O)(μ$_3$-O)$_8$(μ-O)$_8$(O$^t$Bu)$_{16}$) as a white solid. Yield quantity: 0.55 g (yield: 44%).

$^1$H NMR (500 MHz, C$_6$D$_6$) δ 1.71 (s, 36H), 1.68 (s, 36H), 1.67 (s, 3611), 1.58 (s, 36H).
$^{13}$C NMR (125 MHz, C$_6$D$_6$) δ 83.1, 83.0, 82.6, 82.1, 32.5, 31.7, 31.5, 31.2.

A solution prepared by dissolving 33.3 mg of Nb$_{10}$(μ$_4$-O)(μ$_3$-O)$_8$(μ-O)$_8$(O$^t$Bu)$_{16}$ obtained above in 2.0 mL of diisopropyl ether was put in a 2-mL vial tube, and this vial tube was placed in a 20-mL vial tube containing 1.2 mL of acetonitrile. The 20-mL vial tube was tightly closed and left standing for 6 days to obtain a colorless plate-like single crystal.

The crystal of the Nb$_{10}$(μ$_4$-O)(μ$_3$-O)$_8$(μ-O)$_8$(O$^t$Bu)$_{16}$ obtained was analyzed using a single-crystal X-ray structure analyzer (Rigaku Imaging Plate Single-Crystal Automatic X-Ray Structure Analyzer, R-AXIS RAPID II) to determine the molecular structure and the crystal structure. FIG. 1 shows an ORTEP (Oak Ridge Thermal Ellipsoid Program) drawing of the analysis results. The final R value in the structure analysis and refinement was 0.06. The final Rw value was 0.12. In FIG. 1, depiction of the terminal methyl group of a tert-butyloxy group, the diisopropyl ether molecule as a crystallization solvent, and all hydrogen atoms is omitted.

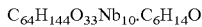 Composition formula:

Crystal system: orthorhombic
Space group: Pnnn (#48)
Z: 2
Calculation density: 1.498 g/cm$^3$
Lattice constant: a=14.07 Å, b=14.80 Å, c=26.33 Å, α=β=γ=90°

From these measurement results, the product Nb$_{10}$(μ$_4$-O)(μ$_3$-O)$_8$(μ-O)$_8$(O$^t$Bu)$_{16}$ obtained by the reaction above was found to have a structure where 10 niobium atoms are crosslinked by 17 oxygen atoms and 16 tert-butyloxy groups are bonded therearound. In addition, it was found that Nb$_{10}$(μ$_4$-O)(μ$_3$-O)$_8$(μ-O)$_8$(O$^t$Bu)$_{16}$ and diisopropyl ether are contained in a molar ratio of 1:1 in the crystal.

Example-2

[Chem. 20]

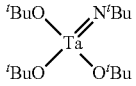

A solution prepared by mixing 2.48 g (5.26 mmol) of (tert-butylimido)tri(tert-butyloxo)tantalum (Ta(N$^t$Bu)(O$^t$Bu)$_3$) and 3 mL of toluene was put in a reaction vessel and freeze-deaerated, and an oxygen-argon mixed gas (oxygen:argon=20 mol %:80 mol %) filling a balloon having an inner volume of 5 liter was introduced into the reaction vessel. After refluxing the solution for 187 hours, volatile components were removed from the reaction solution under reduced pressure, and soluble components were extracted by adding 3 mL of toluene to the remaining solid. Subsequently, 24 mL of acetonitrile was added to the extraction liquid to precipitate a crude product, and the crude product was washed with 8 mL of acetonitrile three times. The crude product was again dissolved in 5 mL of toluene to form a uniform solution, and 40 mL of acetonitrile was added thereto to precipitate a white solid. The white solid was washed with 3 mL of acetonitrile three times and then dried under reduced pressure to obtain hexadecakis(tert-butyloxo)(μ$_4$-oxo)octakis(μ$_3$-oxo)octakis(μ-oxo)decatantalum (Ta$_{10}$(μ$_4$-O)(μ$_3$-O)$_8$(μ-O)$_8$(O$^t$Bu)$_{16}$) as a white solid. Yield quantity: 0.90 g (yield: 53%).

$^1$H NMR (500 MHz, C$_6$D$_6$) δ 1.69 (s, 36H), 1.66 (s, 36H), 1.65 (s, 36H), 1.59 (s, 3611).
$^{13}$C NMR (125 MHz, C$_6$D$_6$) δ 82.2, 81.3$_0$, 81.2$_7$, 79.9, 32.6, 32.0, 31.9, 31.6.

34.0 mg of Ta$_{10}$(μ$_4$-O)(μ$_3$-O)$_8$(μ-O)$_8$(O$^t$Bu)$_{16}$ obtained above was dissolved in 0.7 mL of diisopropyl ether, and the resulting solution was put in a 2-mL vial tube. This vial tube was placed in a 20-mL vial tube containing 0.7 mL of acetonitrile, and the 20-mL vial tube was tightly closed and left standing for 3 days to obtain a colorless needle-like single crystal.

Figure 2:
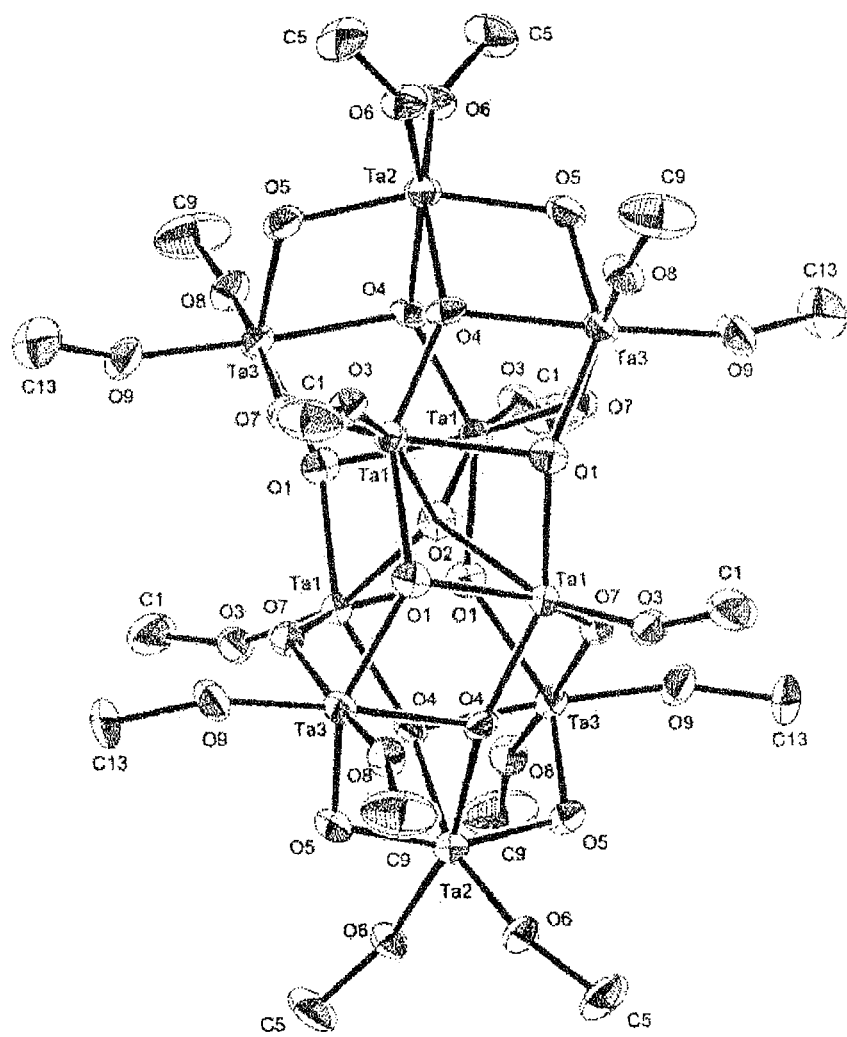
FIG. 2 is a view showing the molecular structure as the result of single-crystal X-ray structure analysis of the crystal obtained in Example 2; in the Figure, the depiction of the terminal methyl group of a tert-butyloxy group, the diisopropyl ether molecule as a crystallization solvent, and all hydrogen atoms is omitted.

The crystal of the Ta$_{10}$(μ$_4$-O)(μ$_3$-O)$_8$(μ-O)$_8$(O$^t$Bu)$_{16}$ obtained was analyzed using a single-crystal X-ray structure analyzer (Rigaku Imaging Plate Single-Crystal Automatic X-Ray Structure Analyzer, R-AXIS RAPID) to determine the molecular structure and the crystal structure. FIG. 2 shows an ORTEP drawing of the analysis results. The final R value in the structure analysis and refinement was 0.11. The final Rw value was 0.24. In FIG. 2, depiction of the terminal methyl group of a tert-butyloxy group, the diisopropyl ether molecule as a crystallization solvent, and all hydrogen atoms is omitted.

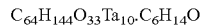 Composition formula:

Crystal system: orthorhombic
Space group: Pnnn (#48)
Z: 2
Calculation density: 2.044 g/cm$^3$
Lattice constant: a=14.00 Å, b=14.80 Å, c=26.29 Å, α=β=γ=90°

From these measurement results, the product Ta$_{10}$(μ$_4$-O)(μ$_3$-O)$_8$(μ-O)$_8$(O$^t$Bu)$_{16}$ obtained by the reaction above was found to have a structure where 10 tantalum atoms are crosslinked by 17 oxygen atoms and 16 tert-butyloxy groups are bonded therearound. In addition, it was found that $Ta_{10}(\mu_4\text{-}O)(\mu_3\text{-}O)_8(\mu\text{-}O)_8(O^tBu)_{16}$ and diisopropyl ether are contained in a molar ratio of 1:1 in the crystal.

Example-3

In an argon atmosphere, 0.04 g of $Nb_{10}(\mu_4\text{-}O)(\mu_3\text{-}O)_8(\mu\text{-}O)_8(O^tBu)_{16}$ obtained in Example 1 was dissolved in 0.8 mL of toluene, and insoluble matters were removed by filtration through a syringe filter (SLLGM25NS, manufactured by Millipore, pore size: 0.20 μm) to obtain Film-Forming Material Nb-01.

Example-4

In an argon atmosphere, 0.10 g of $Ta_{10}(\mu_4\text{-}O)(\mu_3\text{-}O)_8(\mu\text{-}O)_8(O^tBu)_{16}$ obtained in Example 2 was dissolved in 2.0 mL of toluene, and insoluble matters were removed by filtration through a syringe filter (SLLGM25NS, manufactured by Millipore, pore size: 0.20 μm) to obtain Film-Forming Material Ta-01.

Examples 5 to 10

Each of the film-forming materials produced by the methods described in Examples 3 and 4 was coated on a surface of a Corning glass 1737 substrate by the spin coating method, and the substrate was heated while raising the temperature from room temperature to 110° C. at a rate of 20° C./min and further heat-treated for 30 minutes by keeping the temperature at 110° C. (in Table 1, Heat Treatment Temperature 1). Thereafter, the substrate was cooled to room temperature, then again heated while raising the temperature to 200° C. at a rate of 100° C./min, and further heat-treated for 30 minutes at 200° C., 400° C. or 700° C. (in Table 1, Heat Treatment Temperature 2) to manufacture a Group 5 metal oxide film. The evaluation results of the obtained Group 5 metal oxide films are shown in Table 1. Here, the rotation conditions of the spin coating method in these Examples were a rotation speed of 2,000 rpm and a treatment time of 30 seconds. The film thickness and refractive index were determined by multilayer film analysis of the spectrum at a wavelength of 300 to 800 nm measured using an ellipsometer (MEL-30S, manufactured by JASCO Corporation). The refractive index shown in Table 1 is the value measured by allowing incidence of visible light at a wavelength of 634 nm.

The Group 5 metal oxide films of niobium or tantalum obtained in Examples-5 to 10 have a large refractive index and therefore, are suitable, for example, as a transparent electroconductive film, a high-dielectric-constant film, an insulating film, an antireflection film, a hardcoat material, a scratch repairing material for glass, etc., a gas barrier material, and a photocatalytic member.

TABLE 1

| Example | Film-Forming Material | Heat Treatment Temperature 1 | Heat Treatment Temperature 2 | Film Thickness (nm) | Refractive Index |
|---|---|---|---|---|---|
| Example 5 | Nb-01 | 110° C. | 200° C. | 37 | 1.73 |
| Example 6 | Nb-01 | 110° C. | 400° C. | 37 | 1.75 |
| Example 7 | Nb-01 | 110° C. | 700° C. | 31 | 1.76 |
| Example 8 | Ta-01 | 110° C. | 200° C. | 54 | 1.58 |
| Example 9 | Ta-01 | 110° C. | 400° C. | 45 | 1.53 |
| Example 10 | Ta-01 | 110° C. | 700° C. | 43 | 1.57 |

Example 11

[Chem. 21]

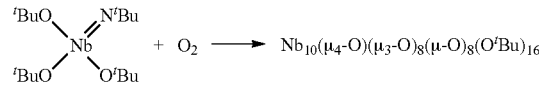

A solution prepared by mixing 1.05 g (2.74 mmol) of (tert-butylimido)tri(tert-butyloxo)niobium $(Nb(N^tBu)(O^tBu)_3)$ and 5 mL of xylene was put in an autoclave having an inner volume of 65 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 150° C. for 19 hours, and the reaction solution was diluted by adding 10 mL of toluene. Subsequently, 50 mL of acetonitrile was added thereto to precipitate a crude product, and the supernatant was removed. The crude product was washed with 5 mL of acetonitrile and then dried under reduced pressure. The residue was dissolved in 5 mL of THF, and 15 mL of acetonitrile was added to the resulting solution to produce a precipitate. After removing the supernatant, the residue was washed with 10 mL of acetonitrile and then dried under reduced pressure to obtain a white solid. Yield quantity: 0.24 g (yield: 37%). The white solid was dissolved in $C_6D_6$, and $^1H$ NMR and $^{13}C$ NMR were measured, as a result, the white solid was identified as hexadecakis(tert-butyloxo)($\mu_4$-oxo)octakis($\mu_3$-oxo)octakis($\mu$-oxo)decaniobium $(Nb_{10}(\mu_4\text{-}O)(\mu_3\text{-}O)_8(\mu\text{-}O)_8(O^tBu)_{16})$.

Reference Example-3

[Chem. 22]

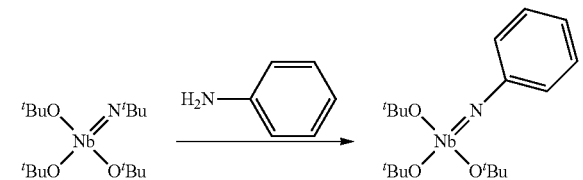

To a solution prepared by mixing 10.52 g (27.44 mmol) of (tert-butylimido)tri(tert-butyloxo)niobium $(Nb(N^tBu)(O^tBu)_3)$ and 5 mL of toluene, 13.00 g (139.6 mmol) of aniline was added and the mixture was stirred at room temperature for 26 hours. The yellow reaction solution was concentrated under reduced pressure and then distilled (distillation temperature: 118° C., back pressure: $3.7 \times 10^1$ Pa) to obtain (phenylimido)tri(tert-butyloxo)niobium $(Nb(NPh)(O^tBu)_3)$ as a yellow solid. Yield quantity: 10.50 g (yield: 95%).

$^1$H NMR (500 MHz, C$_6$D$_6$) δ 7.28 (d, J=8.2 Hz, 2H), 7.15 (t, J=8.2 Hz, 2H), 6.84 (t, J=7.8 Hz, 1H), 1.37 (s, 27H).

$^{13}$C NMR (125 MHz, C$_6$D$_6$) δ 129.3, 128.9, 124.6, 122.5, 79.7, 32.5.

Example-12

[Chem. 23]

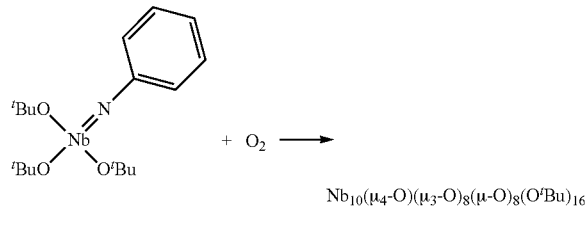

A solution prepared by mixing 1.09 g (2.71 mmol) of (phenylimido)tri(tert-butyloxo)niobium (Nb(NPh)(O$^t$Bu)$_3$) and 5 mL of xylene was put in an autoclave having an inner volume of 65 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 150° C. for 8 hours and 45 minutes, and the reaction solution was diluted by adding 10 mL of toluene. Subsequently, 30 mL of acetonitrile was added thereto to precipitate a crude product, and the supernatant was removed. The crude product was dissolved in 10 mL of toluene, and onto the upper part of the resulting solution, 15 mL of acetonitrile was added/deposited and the solution was left standing to precipitate a colorless block-like crystal. After removing the supernatant, the crystal was washed with 5 mL of acetonitrile and then dried under reduced pressure to obtain a white solid. Yield quantity: 0.28 g (yield: 43%). The white solid was dissolved in C$_6$D$_6$, and $^1$H NMR and $^{13}$C NMR were measured, as a result, the white solid was identified hexadecakis(tert-butyloxo)(μ$_4$-oxo)octakis(μ$_3$-oxo)octakis(μ-oxo)decaniobium (Nb$_{10}$(μ$_4$-O)(μ$_3$-O)$_8$(μ-O)$_8$(O$^t$Bu)$_{16}$).

Example-13

[Chem. 24]

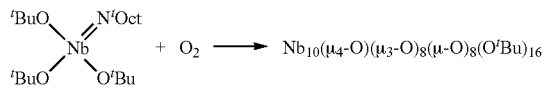

A solution prepared by mixing 1.00 g (2.27 mmol) of (1,1,3,3-tetramethylbutylimido)tri(tert-butyloxo)niobium (Nb(N$^t$Oct)(O$^t$Bu)$_3$) and 5 mL of xylene was put in an autoclave having an inner volume of 65 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 150° C. for 15 hours, and the solvent was removed by distillation under reduced pressure. The residue was dissolved in 5 mL of toluene, and 30 mL of acetonitrile was added to the resulting solution to precipitate a crude product. After removing the supernatant, the precipitate was dried under reduced pressure. The residue was dissolved in 7.5 mL of toluene, and onto the upper part of the resulting solution, 15 mL of acetonitrile was added/deposited and the solution was left standing to precipitate a colorless block-like crystal. After removing the supernatant, the precipitate was dried under reduced pressure to obtain a white solid. Yield quantity: 0.114 g (yield: 21%). The white solid was dissolved in C$_6$D$_6$, and $^1$H NMR and $^{13}$C NMR were measured, as a result, the white solid was identified as hexadecakis(tert-butyloxo)(μ$_4$-oxo)octakis(μ$_3$-oxo)octakis(μ-oxo)decaniobium (Nb$_{10}$(μ$_4$-O)(μ$_3$-O)$_8$(μ-O)$_8$(O$^t$Bu)$_{16}$).

Example-14

[Chem. 25]

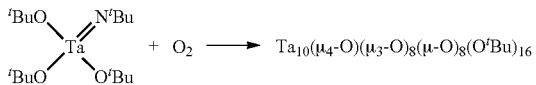

A solution prepared by mixing 1.28 g (2.72 mmol) of (tert-butylimido)tri(tert-butyloxo)tantalum (Ta(N$^t$Bu)(O$^t$Bu)$_3$) and 5 mL of xylene was put in an autoclave having an inner volume of 65 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 150° C. for 12 hours, and the solvent was removed by distillation under reduced pressure. The residue was dissolved in 1.5 mL of toluene, and 25 mL of acetonitrile was added to the resulting solution to precipitate a crude product. After removing the supernatant, the residue was washed with 5 mL of acetonitrile two times and then dried under reduced pressure. The residue was dissolved in 7 mL of THF, and onto the upper part of the resulting solution, 10 mL of acetonitrile was added/deposited and the solution was left standing to precipitate a colorless block-like crystal. After removing the supernatant, the precipitate was dried under reduced pressure to obtain a white solid. Yield quantity: 0.68 g (yield: 77%). The white solid was dissolved in C$_6$D$_6$, and $^1$H NMR and $^{13}$C NMR were measured, as a result, the white solid was identified as hexadecakis(tert-butyloxo)(μ$_4$-oxo)octakis(μ$_3$-oxo)octakis(μ-oxo)decatantalum (Ta$_{10}$(μ$_4$-O)(μ$_3$-O)$_8$(μ-O)$_8$(O$^t$Bu)$_{16}$).

Example 15

[Chem. 26]

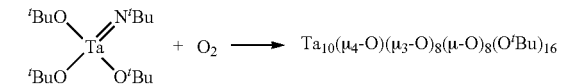

A solution prepared by mixing 1.31 g (2.78 mmol) of (tert-butylimido)tri(tert-butyloxo)tantalum (Ta(N$^t$Bu)(O$^t$Bu)$_3$) and 10 mL of benzotrifluoride was put in an autoclave having an inner volume of 120 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 110° C. for 24 hours, and the solvent was removed by distillation under reduced pressure. The residue was dissolved in 7.5 mL of toluene, and 20 mL of acetonitrile was added to the resulting solution to precipitate a crude product. After removing the supernatant, the crude product was washed with 5 mL of acetonitrile three times and then dried under reduced pressure to obtain a white solid. Yield quantity: 0.21 g (yield: 23%). The white solid was dissolved in $C_6D_6$, and $^1H$ NMR and $^{13}C$ NMR were measured, as a result, the white solid was identified as hexadecakis(tert-butyloxo)($\mu_4$-oxo)octakis($\mu_3$-oxo)octakis ($\mu$-oxo)decatantalum ($Ta_{10}(\mu_4$-O$)(\mu_3$-O$)_8(\mu$-O$)_8(O^tBu)_{16}$).

Example-16

[Chem. 27]

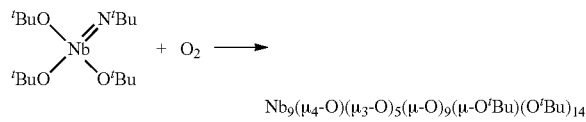

$Nb_9(\mu_4$-O$)(\mu_3$-O$)_5(\mu$-O$)_9(\mu$-O$^tBu)(O^tBu)_{14}$

A solution prepared by mixing 0.966 g (2.52 mmol) of (tert-butylimido)tri(tert-butyloxo)niobium ($Nb(N^tBu)(O^tBu)_3$) and 5 mL of toluene was put in an autoclave having an inner volume of 65 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 110° C. for 17 hours, then depressurized, again pressurized to 0.50 MPa with an oxygen-argon mixed gas (oxygen:argon=20 mol %:80 mol %), and heated at 110° C. for 14.5 hours. After removing volatile components from the reaction solution under reduced pressure, the residue was dissolved in 5 mL of toluene, and 25 mL of acetonitrile was added to the resulting solution to precipitate a crude product. After removing the supernatant, the crude product was washed with 10 mL of acetonitrile three times and then dried under reduced pressure. Soluble components were extracted by adding 12 mL of toluene to the residue, and onto the upper part of the extraction liquid, 7.5 mL of acetonitrile was deposited and the solution was left standing to precipitate a byproduct as a colorless crystal. The supernatant was sampled, and volatile components were removed under reduced pressure. The residue was dissolved in 7.5 mL of toluene, and onto the upper part of the resulting solution, 6 mL of acetonitrile was deposited and the solution was left standing to obtain a colorless block-like single crystal. The supernatant was removed, and the residue was dried under reduced pressure to obtain ($\mu$-tert-butyloxo)tetradecakis (tert-butyloxo)($\mu_4$-oxo)pentakis($\mu_3$-oxo)nonakis($\mu$-oxo)nonaniobium ($Nb_9(\mu_4$-O$)(\mu_3$-O$)_5(\mu$-O$)_9(\mu$-O$^tBu)(O^tBu)_{14}$) as a white solid. Yield quantity: 0.112 g (yield: 18%).

$^1H$ NMR (500 MHz, $C_6D_6$) δ 1.84 (s, 9H), 1.79 (s, 9H), 1.75$_3$ (s, 9H), 1.75$_0$ (s, 9H), 1.74 (s, 9H), 1.70 (s, 9H), 1.69 (s, 9H), 1.64$_2$ (s, 9H), 1.63$_7$ (s, 9H), 1.63 (s, 9H), 1.61$_8$ (s, 9H), 1.61$_5$ (s, 9H), 1.58 (s, 9H), 1.50 (s, 9H), 1.44 (s, 9H).

Figure 3:
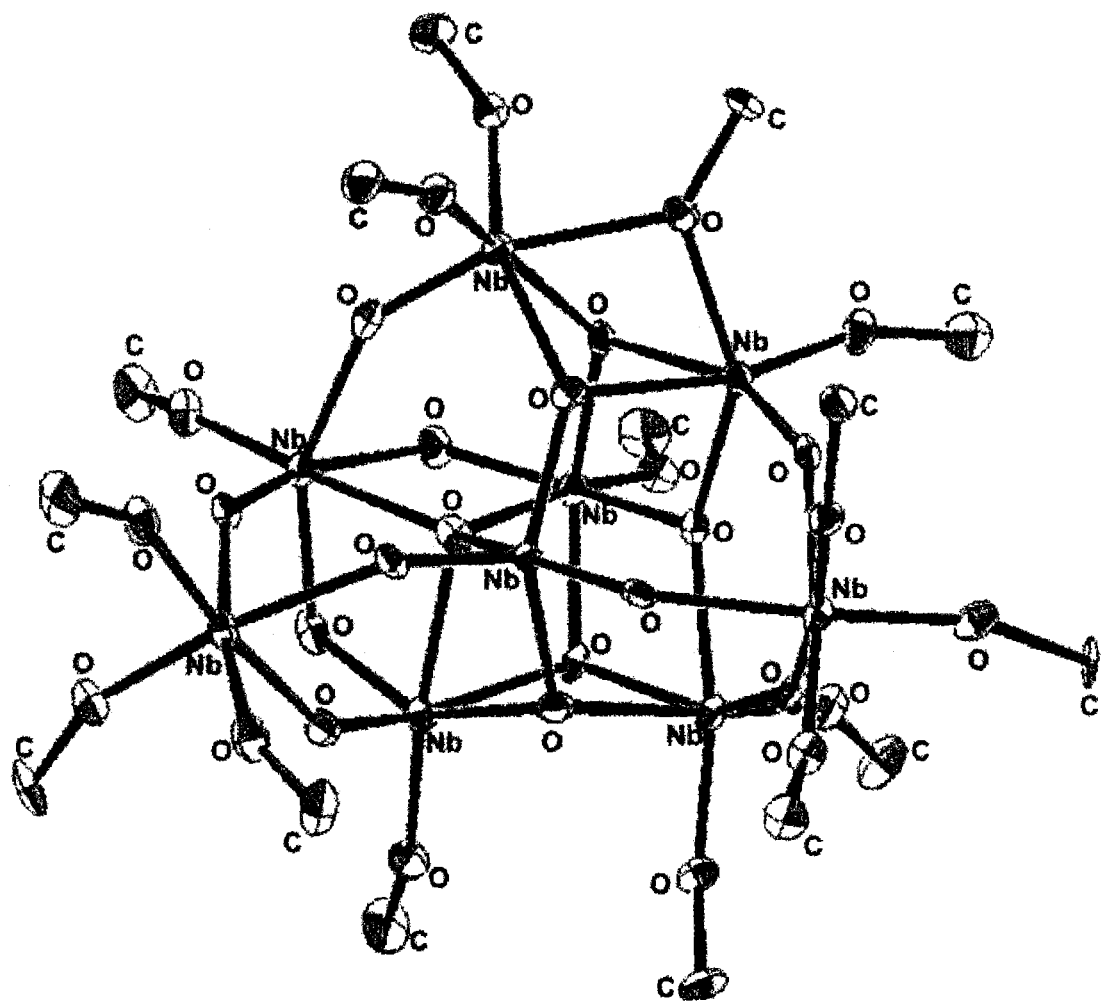
FIG. 3 is a view showing the molecular structure as the result of single-crystal X-ray structure analysis of the crystal obtained in Example 16; in the Figure, the depiction of the terminal methyl group of a tert-butyloxy group, the toluene molecule as a crystallization solvent, and all hydrogen atoms is omitted.

The colorless block-like single crystal of $Nb_9(\mu_4$-O$)(\mu_3$-O$)_5(\mu$-O$)_9(\mu$-O$^tBu)(O^tBu)_{14}$ obtained above was analyzed using a single-crystal X-ray structure analyzer (Rigaku Imaging Plate Single-Crystal Automatic X-Ray Structure Analyzer, R-AXIS RAPID II) to determine the molecular structure and the crystal structure. FIG. 3 shows an ORTEP (Oak Ridge Thermal Ellipsoid Program) drawing of the analysis results. The final R value in the structure analysis and refinement was 0.08. The final Rw value was 0.09. In FIG. 3, depiction of the terminal methyl group of a tert-butyloxy group, the toluene molecule as a crystallization solvent, and all hydrogen atoms is omitted.

Composition formula: $C_{60}H_{135}O_{30}Nb_9 \cdot C_{14}H_{16}$

Crystal system: monoclinic
Space group: P2$_1$/c (#14)
Z: 4
Calculation density: 1.501 g/cm$^3$
Lattice constant: a=23.61 Å, b=16.78 Å, c=25.41 Å, α=γ=90°, β=95.22°

From these measurement results, the product $Nb_9(\mu_4$-O$)(\mu_3$-O$)_5(\mu$-O$)_9(\mu$-O$^tBu)(O^tBu)_{14}$ obtained by the reaction above was found to have a structure where 9 niobium atoms are crosslinked by 15 oxygen atoms and 15 tert-butyloxy groups are bonded therearound. In addition, it was found that $Nb_9(\mu_4$-O$)(\mu_3$-O$)_5(\mu$-O$)_9(\mu$-O$^tBu)(O^tBu)_{14}$ and toluene are contained in a molar ratio of 1:2 in the crystal.

Example-17

[Chem. 28]

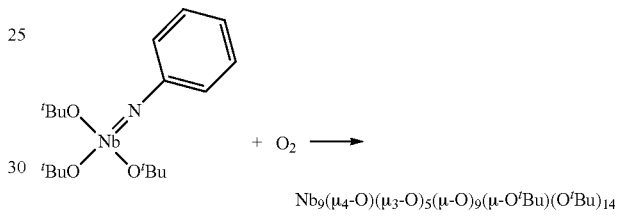

$Nb_9(\mu_4$-O$)(\mu_3$-O$)_5(\mu$-O$)_9(\mu$-O$^tBu)(O^tBu)_{14}$

A solution prepared by mixing 0.609 g (1.51 mmol) of (phenylimido)tri(tert-butyloxo)niobium ($Nb(NPh)(O^tBu)_3$) and 5 mL of xylene was put in an autoclave having an inner volume of 150 mL and being displaced by an oxygen-argon mixed gas (oxygen:argon=20 mol %:80 mol %), and then pressurized to 0.50 MPa with an oxygen-argon mixed gas (oxygen:argon=20 mol %:80 mol %). The solution was heated at 150° C. for 2 hours, and volatile components were removed from the reaction solution under reduced pressure. The residue was dissolved in $C_6D_6$, and $^1H$ NMR was measured, as a result, it was confirmed that ($\mu$-tert-butyloxo) tetradecakis(tert-butyloxo)($\mu_4$-oxo)pentakis($\mu_3$-oxo)nonakis($\mu$-oxo)nonaniobium ($Nb_9(\mu_4$-O$)(\mu_3$-O$)_5(\mu$-O$)_9(\mu$-O$^tBu)(O^tBu)_{14}$) was produced.

Example-18

[Chem. 29]

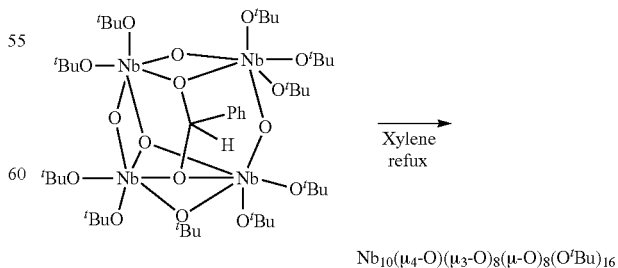

$Nb_{10}(\mu_4$-O$)(\mu_3$-O$)_8(\mu$-O$)_8(O^tBu)_{16}$

A solution prepared by dissolving 0.161 g (0.125 mmol) of ($\mu$-tert-butyloxo)nonakis(tert-butyloxo)($\mu_3$-oxo)tris($\mu$- oxo)(μ₄-benzylidenedioxo)tetraniobium (Nb₄(μ₄-O₂CHPh)(μ₃-O)(μ-O)₃(μ-OᵗBu)(OᵗBu)₉) in 15 mL of xylene was refluxed for 12 hours and 30 minutes. Thereafter, a part of the solution was sampled, and volatile components were removed under reduced pressure. The residue was dissolved in C₆D₆, and ¹H NMR of the resulting solution was measured, as a result, it was confirmed that hexadecakis(tert-butyloxo)(μ₄-oxo)octakis(μ₃-oxo)octakis(μ-oxo)decaniobium (Nb₁₀(μ₄-O)(μ₃-O)₈(μ-O)₈(OᵗBu)₁₆) was produced.

Example-19

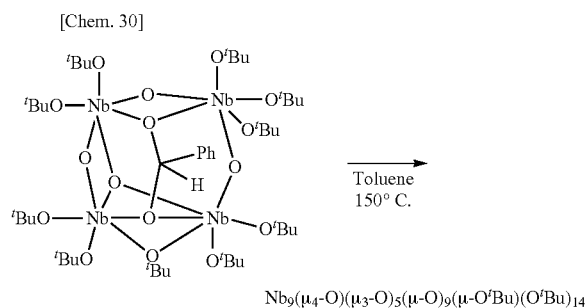

Nb₉(μ₄-O)(μ₃-O)₅(μ-O)₉(μ-OᵗBu)(OᵗBu)₁₄

A solution prepared by dissolving 0.393 g (0.305 mmol) of (μ-tert-butyloxo)nonakis(tert-butyloxo)(μ₃-oxo)tris(μ-oxo)(μ₄-benzylidenedioxo)tetraniobium (Nb₄(μ₄-O₂CHPh)(μ₃-O)(μ-O)₃(μ-OᵗBu)(OᵗBu)₉) in 10 mL of toluene was put in an autoclave having an inner volume of 65 mL and heated at 150° C. for 9 hours. Thereafter, a part of the solution was sampled, and volatile components were removed under reduced pressure. The residue was dissolved in C₆D₆, and ¹H NMR of the resulting solution was measured, as a result, it was confirmed that (μ-tert-butyloxo)tetradecakis(tert-butyloxo)(μ₄-oxo)pentakis(μ₃-oxo)nonakis(μ-oxo)nonaniobium (Nb₉(μ₄-O)(μ₃-O)₅(μ-O)₉(μ-OᵗBu)(OᵗBu)₁₄) was produced.

Example-20

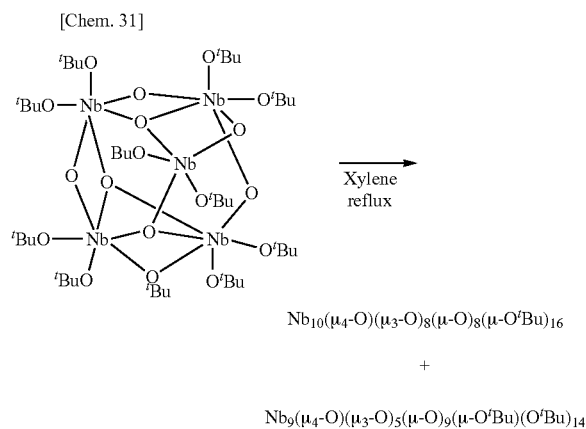

Nb₁₀(μ₄-O)(μ₃-O)₈(μ-O)₈(μ-OᵗBu)₁₆

+

Nb₉(μ₄-O)(μ₃-O)₅(μ-O)₉(μ-OᵗBu)(OᵗBu)₁₄

A solution prepared by dissolving 0.307 g (0.225 mmol) of (μ-tert-butyloxo)decakis(tert-butyloxo)tris(μ₃-oxo)tetrakis(μ-oxo)pentaniobium (Nb₅(μ₃-O)₃(μ-O)₄(μ-OᵗBu)(OᵗBu)₁₀) in 6 mL of xylene was refluxed for 3 hours and 20 minutes. Thereafter, a part of the solution was sampled, and volatile components were removed under reduced pressure. The residue was dissolved in C₆D₆, and ¹H NMR of the resulting solution was measured, as a result, it was confirmed that hexadecakis(tert-butyloxo)(μ₄-oxo)octakis(μ₃-oxo)octakis(μ-oxo)decaniobium (Nb₁₀(μ₄-O)(μ₃-O)₈(μ-O)₈(OᵗBu)₁₆) and (μ-tert-butyloxo)tetradecakis(tert-butyloxo)(μ₄-oxo)pentakis(μ₃-oxo)nonakis(μ-oxo)nonaniobium (Nb₉(μ₄-O)(μ₃-O)₅(μ-O)₉(μ-OᵗBu)(OᵗBu)₁₄) were produced in a molar ratio of 1:3.

Reference Example-4

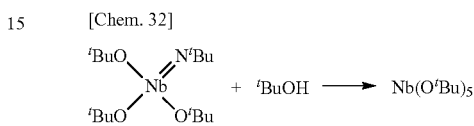

To a solution prepared by mixing 10.51 g (27.42 mmol) of (tert-butylimido)tri(tert-butyloxo)niobium (Nb(NᵗBu)(OᵗBu)₃) and 25 mL of hexane, 4.17 g (56.26 mmol) of tert-butyl alcohol was added and the mixture was stirred at room temperature for 1 hour and thereafter, volatile components were removed under reduced pressure to obtain pentakis(tert-butyloxo)niobium as a white solid. Yield quantity: 12.28 g (yield: 98%).

¹H NMR (500 MHz, C₆D₆) δ 1.48 (br s, half-value width 15.93 Hz, 45H).

¹³C NMR (125 MHz, C₆D₆) δ 79.8, 31.6.

Elemental Analysis (C, H, N):

TABLE 2

| Element | Measured Value (%) | Theoretical Value(%) |
| --- | --- | --- |
| C | 51.8 | 52.4 |
| H | 10.1 | 9.9 |
| N | <0.3 | 0 |
| O | — | 20.3 |
| Nb | — | 17.5 |

Example-21

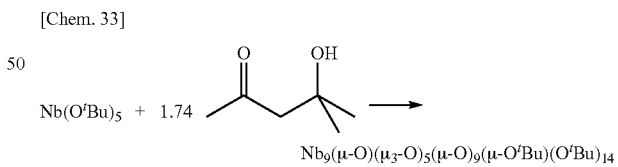

Nb₉(μ-O)(μ₃-O)₅(μ-O)₉(μ-OᵗBu)(OᵗBu)₁₄

To a solution prepared by dissolving 0.249 g (0.543 mmol) of pentakis(tert-butyloxo)niobium in 5 mL of toluene, 1.438 g (0.947 mmol) of a 7.65 wt % diacetone alcohol-toluene solution was added and the mixture was stirred at room temperature for 22 hours. Thereafter, a part of the solution was sampled, and volatile components were removed under reduced pressure. The residue was dissolved in C₆D₆, and ¹H NMR of the resulting solution was measured, as a result, it was confirmed that (μ-tert-butyloxo)tetradecakis(tert-butyloxo)(μ₄-oxo)pentakis(μ₃-oxo)nonakis(μ-oxo)nonaniobium (Nb₉(μ₄-O)(μ₃-O)₅(μ-O)₉(μ-OᵗBu)(OᵗBu)₁₄) was produced.

Example-22

In an argon atmosphere, 0.04 g of $Nb_9(\mu_4\text{-}O)(\mu_3\text{-}O)_5(\mu\text{-}O)_9(\mu\text{-}O^tBu)(O^tBu)_{14}$ obtained in Example 16 was dissolved in 0.8 mL of toluene, and insoluble matters were removed by filtration through a syringe filter (SLLGM25NS, manufactured by Millipore, pore size: 0.20 μm) to obtain Film-Forming Material Nb-02.

Examples-23 to 25

Film-Forming Material Nb-02 produced by the method described in Example 22 was coated on a surface of a Corning glass 1737 substrate by the spin coating method, and the substrate was heated while raising the temperature from room temperature to 110° C. at a rate of 20° C./min and further heat-treated for 30 minutes by keeping the temperature at 110° C. (in Table 3, Heat Treatment Temperature 1). Thereafter, the substrate was cooled to room temperature, then again heated while raising the temperature to 200° C. at a rate of 100° C./min, and further heat-treated for 30 minutes at 200° C., 400° C. or 700° C. (in Table 3, Heat Treatment Temperature 2) to manufacture a film. Each of the thus-manufactured films was analyzed by X-ray photoelectron spectroscopy. The evaluation results of the obtained Group 5 metal oxide films are shown in Table 3. Here, the rotation conditions of the spin coating method in these Examples were a rotation speed of 2,000 rpm and a treatment time of 30 seconds.

TABLE 3

| Example | Film-Forming Material | Heat Treatment Temperature 1 | Heat Treatment Temperature 2 | X-Ray Photoelectron Spectroscopy, detected/not detected (Nb and O) |
|---|---|---|---|---|
| Example 23 | Nb-02 | 110° C. | 200° C. | detected |
| Example 24 | Nb-02 | 110° C. | 400° C. | detected |
| Example 25 | Nb-02 | 110° C. | 700° C. | detected |

The niobium oxide films obtained in Examples-23 to 25 are suitable, for example, as a transparent electroconductive film, a high-dielectric-constant film, an insulating film, an antireflection film, a hardcoat material, a scratch repairing material for glass, etc., a gas barrier material, and a photocatalytic member.

Example-26

[Chem. 34]

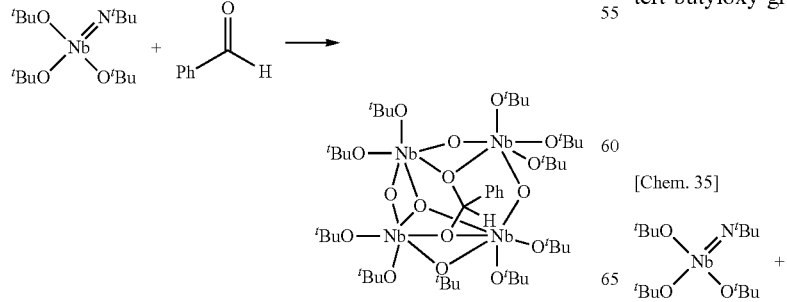

Example-27

To a solution prepared by mixing 5.17 g (13.5 mmol) of (tert-butylimido)tri(tert-butyloxo)niobium ($Nb(N^tBu)(O^tBu)_3$) and 25 mL of toluene, 1.50 g (14.1 mmol) of benzaldehyde was added and the mixture was stirred at room temperature for 3 hours and 20 minutes and thereafter, 1.54 g (14.5 mmol) of benzaldehyde was further added and the mixture was stirred at room temperature for 2 hours. Subsequently, 75 mL of acetonitrile was added to produce a white precipitate. After removing the supernatant, the residue was washed with 25 mL of acetonitrile and then dried under reduced pressure to obtain (μ-tert-butyloxo)nonakis(tert-butyloxo)(μ$_3$-oxo)tris(μ-oxo)(μ$_4$-benzylidenedioxo)tetraniobium ($Nb_4(\mu_4\text{-}O_2CHPh)(\mu_3\text{-}O)(\mu\text{-}O)_3(\mu\text{-}O^tBu)(O^tBu)_9$) as a white solid. Yield quantity: 3.00 g (yield: 69%).

$^1$H NMR (500 MHz, $C_6D_6$) δ 8.01 (d, J=7.8 Hz, 2H), 7.77 (s, 1H), 7.36 (dd, J=7.8, 7.3 Hz, 2H), 7.20 (t, J=7.3 Hz, 1H), 1.76 (s, 9H), 1.75 (s, 9H), 1.70 (s, 9H), 1.67 (s, 9H), 1.65 (s, 9H), 1.58 (s, 9H), 1.52 (s, 9H), 1.48 (s, 9H), 1.27 (s, 9H), 1.11 (s, 9H).

Onto the upper part of a solution prepared by dissolving 0.70 g of $Nb_4(\mu_4\text{-}O_2CHPh)(\mu_3\text{-}O)(\mu\text{-}O)_3(\mu\text{-}O^tBu)(O^tBu)_9$ obtained above in 10 mL of toluene, 20 mL of acetonitrile was poured/deposited and the solution was left standing to obtain a colorless block-like single crystal.

The crystal of $Nb_4(\mu_4\text{-}O_2CHPh)(\mu_3\text{-}O)(\mu\text{-}O)_3(\mu\text{-}O^tBu)(O^tBu)_9$ obtained was analyzed using a single-crystal X-ray structure analyzer (Rigaku Imaging Plate Single-Crystal Automatic X-Ray Structure Analyzer, R-AXIS RAPID II) to determine the molecular structure and the crystal structure. FIG. 4 shows an ORTEP (Oak Ridge Thermal Ellipsoid Program) drawing of the analysis results. The final R value in the structure analysis and refinement was 0.064. The final Rw value was 0.178. In FIG. 4, depiction of the terminal methyl group of a tert-butyloxy group and all hydrogen atoms is omitted.

Composition formula: $C_{47}H_{96}O_{16}Nb_4$

Crystal system: monoclinic

Space group: P2$_1$/c (#14)

Z: 4

Calculation density: 1.386 g/cm$^3$

Lattice constant: a=16.67 Å, b=19.34 Å, c=19.16 Å, α=γ=90°, β=91.58°

From these measurement results, the product $Nb_4(\mu_4\text{-}O_2CHPh)(\mu_3\text{-}O)(\mu\text{-}O)_3(\mu\text{-}O^tBu)(O^tBu)_9$ obtained by the reaction above was found to have a structure where 4 niobium atoms are crosslinked by 4 oxygen atoms, one tert-butyloxy group and one benzylidenedioxy group and 9 tert-butyloxy groups are bonded therearound.

Example-27

[Chem. 35]

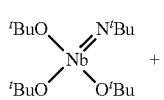

-continued

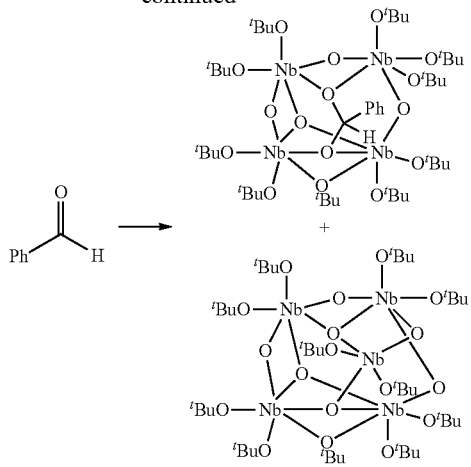

A solution prepared by mixing 0.540 g (1.41 mmol) of (tert-butylimido)tri(tert-butyloxo)niobium (Nb(N$^t$Bu)(O$^t$Bu)$_3$) and 10 mL of toluene was cooled in a dry ice-methanol bath, and a solution prepared by mixing 0.156 g (1.47 mmol) of benzaldehyde and 5 mL of toluene was added thereto over 15 minutes. The resulting solution was raised in the temperature and stirred at room temperature for 41 hours. Thereafter, a part of the solution was sampled, and volatile components were removed under reduced pressure. The residue was dissolved in C$_6$D$_6$, and $^1$H NMR of the resulting solution was measured, as a result, it was confirmed that (μ-tert-butyloxo)nonakis(tert-butyloxo)(μ$_3$-oxo)tris(μ-oxo)(μ$_4$-benzylidenedioxo)tetraniobium (Nb$_4$(μ$_4$-O$_2$CHPh)(μ$_3$-O)(μ-O)$_3$(μ-O$^t$Bu)(O$^t$Bu)$_9$) and (μ-tert-butyloxo)decakis(tert-butyloxo)tris(μ-oxo)tetrakis(μ-oxo)pentaniobium (Nb$_5$(μ$_3$-O)$_3$(μ-O)$_4$(μ-O$^t$Bu)(O$^t$Bu)$_{10}$) were produced in a molar ratio of 1.0:1.4.

Example-28

[Chem. 36]

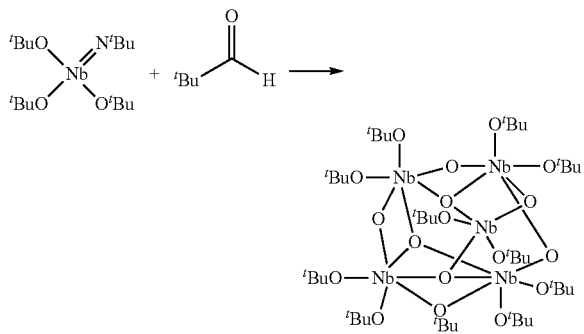

To a solution prepared by mixing 5.086 g (13.27 mmol) of (tert-butylimido)tri(tert-butyloxo)niobium (Nb(N$^t$Bu)(O$^t$Bu)$_3$) and 20 mL of toluene, a solution prepared by mixing 1.120 g (13.01 mmol) of pivalaldehyde and 10 mL of toluene was added thereto dropwise over 10 minutes on an ice bath. After stirring for 2 hours on an ice bath, volatile components were removed under reduced pressure, and the residue was washed with 40 mL of acetonitrile and then dried under reduced pressure. Soluble components were extracted with 15 mL of toluene from the residue, and onto the upper part of the extraction liquid, 35 mL of acetonitrile was deposited and the solution was left standing at 25° C. to precipitate a colorless crystal. The supernatant was removed, and the residue was dried under reduced pressure to obtain (μ-tert-butyloxo)decakis(tert-butyloxo)tris(μ$_3$-oxo)tetrakis(μ-oxo)pentaniobium (Nb$_5$(μ$_3$-O)$_3$(μ-O)$_4$(μ-O$^t$Bu)(O$^t$BU)$_{10}$) as a white solid. Yield quantity: 1.86 g (yield: 51%).

$^1$H NMR (500 MHz, C$_6$D$_6$, 30° C.) δ 1.61 (br), 1.58 (br), 1.51 (br).

$^1$H NMR (500 MHz, C$_6$D$_6$, −40° C.) δ 1.73 (s, 9H), 1.71 (s, 9H), 1.65 (s, 9H), 1.64 (s, 9H), 1.63 (s, 9H), 1.61 (s, 27H), 1.56 (s, 9H), 1.55 (s, 9H), 1.49 (s, 9H).

Onto the upper portion of a solution prepared by dissolving 41.1 mg of Nb$_5$(μ$_3$-O)$_3$(μ$_4$-O)$_4$(μ-O$^t$Bu)(O$^t$Bu)$_{10}$ obtained above in 2.5 mL of toluene, 10 mL of acetonitrile was poured/deposited and the solution was left standing at 25° C. to obtain a colorless block-like single crystal.

The crystal of Nb$_5$(μ$_3$-O)$_3$(μ-O)$_4$(μ-O$^t$Bu)(O$^t$Bu)$_{10}$ obtained was analyzed using a single-crystal X-ray structure analyzer (Rigaku Imaging Plate Single-Crystal Automatic X-Ray Structure Analyzer, R-AXIS RAPID II) to determine the molecular structure and the crystal structure. FIG. 5 shows an ORTEP (Oak Ridge Thermal Ellipsoid Program) drawing of the analysis results. The final R value in the structure analysis and refinement was 0.068. The final Rw value was 0.114. In FIG. 5, depiction of the terminal methyl group of a tert-butyloxy group and all hydrogen atoms is omitted.

C$_{44}$H$_{99}$O$_{18}$Nb$_5$    Composition formula:

Crystal system: monoclinic
Space group: P2$_1$/n (#14)
Z: 4
Calculation density: 1.498 g/cm$^3$
Lattice constant: a=16.90 Å, b=18.63 Å, c=19.46 Å, α=γ=90°, β=91.98°

From these measurement results, the product Nb$_5$(μ$_3$-O)$_3$(μ-O)$_4$(μ-O$^t$Bu)(O$^t$Bu)$_{10}$ obtained by the reaction above was found to have a structure where 5 niobium atoms are crosslinked by 7 oxygen atoms and one tert-butyloxy group and 10 tert-butyloxy groups are bonded therearound.

Example-29

[Chem. 37]

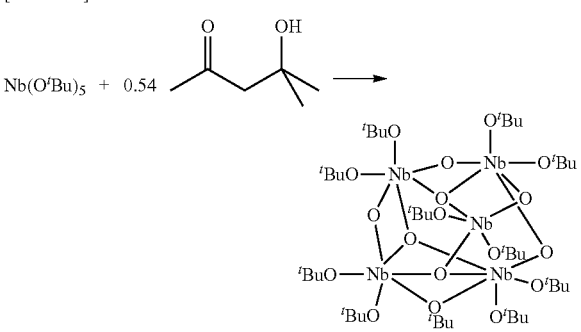

To a solution prepared by dissolving 0.231 g (0.504 mmol) of pentakis(tert-butyloxo)niobium in 5 mL of toluene, 0.413 g (0.272 mmol) of a 7.65 wt % diacetone alcohol-toluene solution was added and stirred at room temperature for 22 hours. Thereafter, a part of the solution was sampled, and volatile components were removed under reduced pressure. The residue was dissolved in $C_6D_6$, and $^1H$ NMR of the resulting solution was measured, as a result, it was confirmed that (μ-tert-butyloxo)decakis(tert-butyloxo)tris(μ$_3$-oxo)tetrakis(μ-oxo)pentaniobium (Nb$_5$(μ$_3$-O)$_3$(μ-O)$_4$(μ-O$^t$Bu)(O$^t$Bu)$_{10}$) was produced.

Example-30

[Chem. 38]

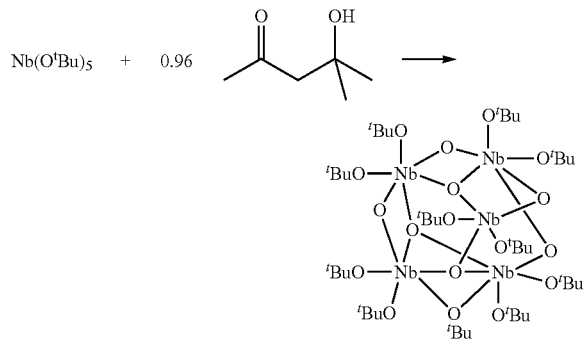

To a solution prepared by dissolving 0.234 g (0.510 mmol) of pentakis(tert-butyloxo)niobium in 5 mL of toluene, 0.747 g (0.492 mmol) of a 7.65 wt % diacetone alcohol-toluene solution was added and the mixture was stirred at room temperature for 29 hours. Onto the upper part of the resulting solution, 10 mL of acetonitrile was poured/deposited and the solution was left standing to obtain a colorless block-like single crystal. The supernatant was removed, and the crystal was dried under reduced pressure to obtain a white solid. Yield quantity: 0.080 g. This white solid was dissolved in $C_6D_6$, and $^1H$ NMR thereof was measured, as a result, it was confirmed that (μ-tert-butyloxo)decakis(tert-butyloxo)tris(μ$_3$-oxo)tetrakis(μ-oxo)pentaniobium (Nb$_5$(μ$_3$-O)$_3$(μ-O)$_4$(μ-O$^t$Bu)(O$^t$Bu)$_{10}$) was produced.

Example-31

In an argon atmosphere, 0.05 g of Nb$_4$(μ$_4$-O$_2$CHPh)(μ$_3$-O)(μ-O)$_3$(μ-O$^t$Bu)(O$^t$Bu)$_9$ obtained in Example 26 was dissolved in 1.0 mL of toluene, and insoluble matters were removed by filtration through a syringe filter (SLLGM25NS, manufactured by Millipore, pore size: 0.20 μm) to obtain Film-Forming Material Nb-03.

Example-32

In an argon atmosphere, 0.09 g of Nb$_5$(μ$_3$-O)$_3$(μ-O)$_4$(μ-O$^t$Bu)(O$^t$Bu)$_{10}$ obtained in Example 28 was dissolved in 1.8 mL of toluene, and insoluble matters were removed by filtration through a syringe filter (SLLGM25NS, manufactured by Millipore, pore size: 0.20 μm) to obtain Film-Forming Material Nb-04.

Examples-33 to 38

Each of the film-forming materials produced by the methods described in Examples 31 and 32 was coated on a surface of a Corning glass 1737 substrate by the spin coating method, and the substrate was heated while raising the temperature from room temperature to 110° C. at a rate of 20° C./min and further heat-treated for 30 minutes by keeping the temperature at 110° C. (in Table 4, Heat Treatment Temperature 1). Thereafter, the substrate was cooled to room temperature, then again heated while raising the temperature to 200° C. at a rate of 100° C./min, and further heat-treated for 30 minutes at 200° C., 400° C. or 700° C. (in Table 4, Heat Treatment Temperature 2) to manufacture a film. Each of the thus-manufactured films was analyzed by X-ray photoelectron spectroscopy. The evaluation results of the obtained Group 5 metal oxide films are shown in Table 4. Here, the rotation conditions of the spin coating method in these Examples were a rotation speed of 2,000 rpm and a treatment time of 30 seconds.

TABLE 4

| Example | Film-Forming Material | Heat Treatment Temperature 1 | Heat Treatment Temperature 2 | X-Ray Photoelectron Spectroscopy, detected/not detected (Nb and O) |
|---|---|---|---|---|
| Example 33 | Nb-03 | 110° C. | 200° C. | detected |
| Example 34 | Nb-03 | 110° C. | 400° C. | detected |
| Example 35 | Nb-03 | 110° C. | 700° C. | detected |
| Example 36 | Nb-04 | 110° C. | 200° C. | detected |
| Example 37 | Nb-04 | 110° C. | 400° C. | detected |
| Example 38 | Nb-04 | 110° C. | 700° C. | detected |

The niobium oxide films obtained in Examples-33 to 38 are suitable, for example, as a transparent electroconductive film, a high-dielectric-constant film, an insulating film, an antireflection film, a hardcoat material, a scratch repairing material for glass, etc., a gas barrier material, and a photocatalytic member.

Example-39

[Chem. 39]

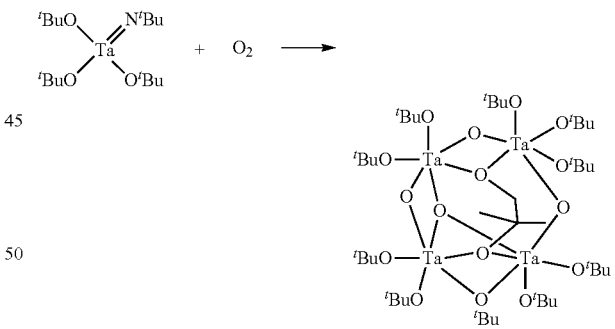

A solution prepared by mixing 3.49 g (7.40 mmol) of (tert-butylimido)tri(tert-butyloxo)tantalum (Ta(N$^t$Bu)(O$^t$Bu)$_3$) and 35 mL of hexane was put in a reaction vessel and freeze-deaerated, and an oxygen-argon mixed gas (oxygen:argon=20 mol %:80 mol %) filling a balloon having an inner volume of 5 liter was introduced into the reaction vessel. After stirring the solution at 25° C. for 3 days, insoluble matters were filtered, and volatile components were removed from the filtrate under reduced pressure. The residue was dissolved in 5 mL of toluene, and 20 mL of acetonitrile was added thereto to precipitate a crude product. The supernatant was removed, and the crude product was dissolved in 8 mL of THF. Onto the upper part of the resulting solution, 15 mL of acetonitrile was poured/deposited and the solution was left standing at 25° C. to produce a white precipitate. After removing the supernatant, the residue was washed with 5 mL of acetonitrile and then dried under reduced pressure. The residue was dissolved in 10 mL of toluene, and onto the upper part of the resulting solution, 5 mL of acetonitrile was poured/deposited and the solution was left standing to precipitate a colorless crystal. The supernatant was removed, and the crystal was washed with 2.5 mL of acetonitrile and dried under reduced pressure. The obtained crystal was dissolved in 8 mL of toluene, and onto the upper part of the resulting solution, 8 mL of acetonitrile was poured/deposited and the solution was left standing to precipitate a colorless crystal. The supernatant was removed, and the residue was dried under reduced pressure to obtain a white solid. Yield quantity: 0.22 g.

Onto the upper part of a solution prepared by dissolving 0.18 g of the white solid obtained above in 6 mL of toluene, 5 mL of acetonitrile was poured/deposited and the solution was left standing at 25° C. to obtain a colorless block-like single crystal.

The obtained crystal was analyzed using a single-crystal X-ray structure analyzer (Rigaku Imaging Plate Single-Crystal Automatic X-Ray Structure Analyzer, R-AXIS RAPID II) to determine the molecular structure and the crystal structure, as a result, the crystal was found to be (μ-tert-butyloxo)nonakis(tert-butyloxo)(μ$_3$-oxo)tris(μ-oxo)(μ$_4$-2-methyl-1,2-propanedioxo)tetratantalum (Ta$_4$(μ$_4$-OCMe$_2$CH$_2$O)(μ$_3$-O)(μ-O)$_3$(μ-O$^t$Bu)(O$^t$Bu)$_9$). FIG. 6 shows an ORTEP (Oak Ridge Thermal Ellipsoid Program) drawing of the analysis results. The final R value in the structure analysis and refinement was 0.11. The final Rw value was 0.22. In FIG. 6, depiction of the terminal methyl group of a tert-butyloxy group and all hydrogen atoms is omitted.

Composition formula: $C_{44}H_{98}O_{16}Ta_4$

Crystal system: monoclinic
Space group: P2$_1$/c (#14)
Z: 4
Calculation density: 3.228 g/cm$^3$
Lattice constant: a=14.86 Å, b=19.69 Å, c=21.39 Å, α=γ=90°, β=103.62°

From these measurement results, the product Ta$_4$(μ$_4$-OCMe$_2$CH$_2$O)(μ$_3$-O)(μ-O)$_3$(μ-O$^t$Bu)(O$^t$Bu)$_9$ obtained by the reaction above was found to have a structure where 4 tantalum atoms are crosslinked by 4 oxygen atoms, one tert-butyloxy group and one 2-methyl-1,2-propanedioxy group and 9 tert-butyloxy groups are bonded therearound.

Example-40

In an argon atmosphere, 0.04 g of the white solid obtained in Example 39 was dissolved in 0.8 mL of toluene, and insoluble matters were removed by filtration through a syringe filter (SLLGM25NS, manufactured by Millipore, pore size: 0.20 μm) to obtain Film-Forming Material Ta-02.

Examples-41 to 43

The film-forming material produced by the method described in Example 40 was coated on a surface of a Corning glass 1737 substrate by the spin coating method, and the substrate was heated while raising the temperature from room temperature to 110° C. at a rate of 20° C./min and further heat-treated for 30 minutes by keeping the temperature at 110° C. (in Table 5, Heat Treatment Temperature 1). Thereafter, the substrate was cooled to room temperature, then again heated while raising the temperature to 200° C. at a rate of 100° C./min, and further heat-treated for 30 minutes at 200° C., 400° C. or 700° C. (in Table 5, Heat Treatment Temperature 2) to manufacture a film. Each of the thus-manufactured films was analyzed by X-ray photoelectron spectroscopy. The evaluation results of the obtained Group 5 metal oxide films are shown in Table 5. Here, the rotation conditions of the spin coating method in these Examples were a rotation speed of 2,000 rpm and a treatment time of 30 seconds.

TABLE 5

| Example | Film-Forming Material | Heat Treatment Temperature 1 | Heat Treatment Temperature 2 | X-Ray Photoelectron Spectroscopy, detected/not detected (Nb and O) |
|---|---|---|---|---|
| Example 41 | Ta-02 | 110° C. | 200° C. | detected |
| Example 42 | Ta-02 | 110° C. | 400° C. | detected |
| Example 43 | Ta-02 | 110° C. | 700° C. | detected |

The tantalum oxide films obtained in Examples-41 to 43 are suitable, for example, as a transparent electroconductive film, a high-dielectric-constant film, an insulating film, an antireflection film, a hardcoat material, a scratch repairing material for glass, etc., a gas barrier material, and a photocatalytic member.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2012-286956) filed on Dec. 28, 2012, the entirety of which is incorporated herein by way of reference. All references cited herein are incorporated in their entirety.

The invention claimed is:

1. A Group 5 metal oxo-alkoxo complex represented by formula (1), chemical formula (3), chemical formula (4) or chemical formula (5):

$$M_A(\mu_4\text{-}O)_B(\mu_3\text{-}O)_C(\mu\text{-}O)_D(\mu\text{-}O^tBu)_E(O^tBu)_F \quad (1)$$

wherein M represents a niobium atom or a tantalum atom; and A, B, C, D, E and F represent respectively numerical values of 10, 1, 8, 8, 0 and 16 or of 9, 1, 5, 9, 1 and 14:

-continued (5)

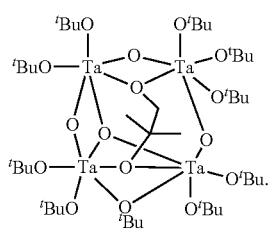

2. The Group 5 metal oxo-alkoxo complex according to claim 1,
wherein the Group 5 metal oxo-alkoxo complex is represented by formula (1).

3. The Group 5 metal oxo-alkoxo complex according to claim 1,
wherein the Group 5 metal oxo-alkoxo complex is represented by formula (1A):

(1A)

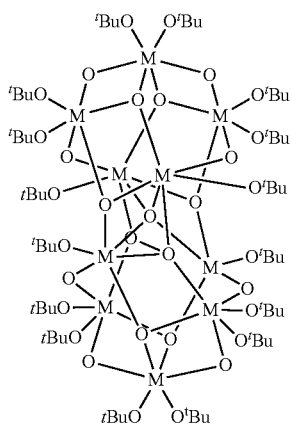

wherein M represents a niobium atom or a tantalum atom, or formula (1B):

(1B)

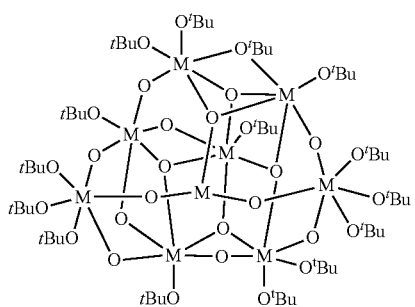

wherein M represents a niobium atom or a tantalum atom.

4. The Group 5 metal oxo-alkoxo complex according to claim 1,
wherein the Group 5 metal oxo-alkoxo complex is represented by chemical formula (3) or chemical formula (4).

5. The Group 5 metal oxo-alkoxo complex according to claim 1,
wherein the Group 5 metal oxo-alkoxo complex is represented by chemical formula (5).

6. A method for producing the Group 5 metal oxo-alkoxo complex according to claim 1, comprising:
reacting a metal imido-trialkoxo complex represented by formula (2):

(2)

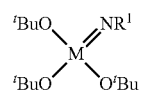

wherein M represents a niobium atom or a tantalum atom; and $R^1$ represents a $C_4$-$C_{12}$ tertiary alkyl group or a phenyl group represented by formula (2Ar):

(2Ar)

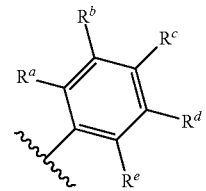

wherein each of $R^a$, $R^b$, $R^c$, $R^d$ and $R^e$ independently represents a hydrogen atom or a $C_1$-$C_6$ alkyl group, which may be substituted,
with one or more oxidants selected from the group consisting of oxygen, air and ozone.

7. A method for producing the Group 5 metal oxo-alkoxo complex according to claim 1, comprising:
heating a Group 5 metal oxo-alkoxo complex represented by chemical formula (3):

(3)

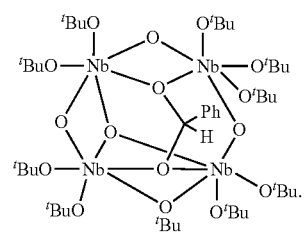

8. A method for producing the Group 5 metal oxo-alkoxo complex according to claim 1, comprising:
heating a Group 5 metal oxo-alkoxo complex represented by chemical formula (4):

(4)

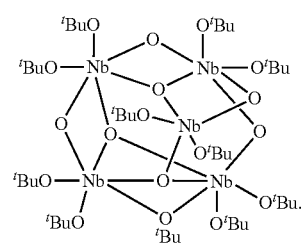

9. A method for producing the Group 5 metal oxo-alkoxo complex according to claim 1, comprising:

reacting pentakis(tert-butyloxo)niobium (Nb(O$^t$Bu)$_5$) with diacetone alcohol.

10. A method for producing the Group 5 metal oxo-alkoxo complex according to claim 1, which is represented by chemical formula (3):

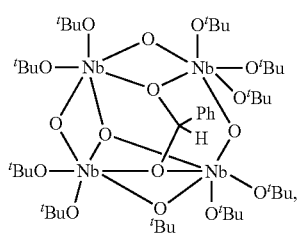

the method comprising:
reacting a metal imido-trialkoxo complex represented by formula (2a-Nb):

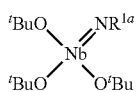

wherein R$^{1a}$ represents a C$_1$-C$_{12}$ alkyl group, with benzaldehyde.

11. A method for producing the Group 5 metal oxo-alkoxo complex according to claim 1, which is represented by chemical formula (4):

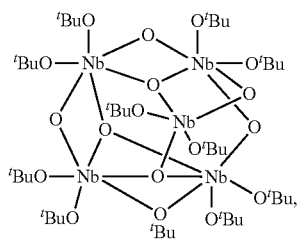

the method comprising:
reacting a metal imido-trialkoxo complex represented by formula (2a-Nb):

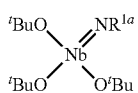

wherein R$^{1a}$ represents a C$_1$-C$_{12}$ alkyl group, with an aldehyde represented by formula (7):

wherein R$^2$ represents a phenyl group or a C$_4$-C$_8$ tertiary alkyl group.

12. A method for producing the Group 5 metal oxo-alkoxo complex according to claim 1, which is represented by chemical formula (5):

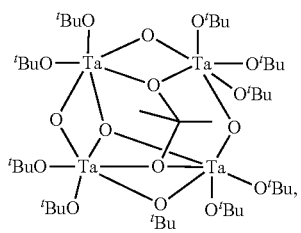

the method comprising:
reacting a metal imido-trialkoxo complex represented by formula (2a-Ta):

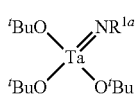

wherein R$^{1a}$ represents a C$_1$-C$_{12}$ alkyl group, with one or more oxidants selected from the group consisting of oxygen, air and ozone, at a temperature of less than 60° C.

13. A film-forming material, comprising:
a Group 5 metal oxo-alkoxo complex represented by formula (A):

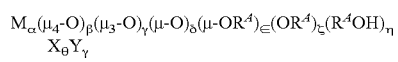

(A)

wherein M represents a niobium atom or a tantalum atom; R$^A$ represents a C$_1$-C$_6$ alkyl group; X represents a C$_1$-C$_8$ alkylenedioxy group that may be substituted with a phenyl group; Y represents a C$_2$-C$_8$ carboxy group that may be substituted with a halogen atom, or an acetylacetonate group; α represents an integer of 3 to 10; β represents 0 or 1; γ represents an integer of 0 to 8; δ represents an integer of 2 to 9; ∈ represents an integer of 0 to 6; ζ represents an integer of 6 to 16; η represents an integer of 0 to 4; θ represents an integer of 0 to 2; and τ represents an integer of 0 to 6, provided that α to τ represent integers satisfying 5α=2(β+γ+δ+θ)+∈+ζ+τ;

and an organic solvent, in a weight ratio of from 1:0.1 to 1:1,000,000.

14. The film-forming material according to claim 13, wherein the Group 5 metal oxo-alkoxo complex represented by formula (A) is a Group 5 metal oxo-alkoxo complex represented by formula (1), chemical formula (3), chemical formula (4) or chemical formula (5):

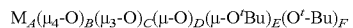

(1)

wherein M represents a niobium atom or a tantalum atom; and A, B, C, D, E and F represent respectively numerical values of 10, 1, 8, 8, 0 and 16 or of 9, 1, 5, 9, 1 and 14:

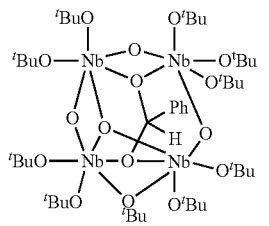
(3)

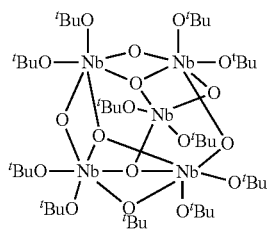
(4)

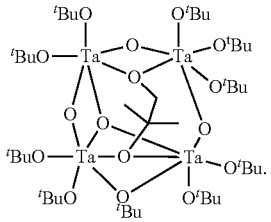
(5)

15. The film-forming material according to claim 13, wherein the organic solvent is an aliphatic hydrocarbon or an aromatic hydrocarbon.

16. A method for manufacturing a Group 5 metal oxide film, comprising:

applying the film-forming material according to claim 13 on a surface of a substrate; and heat-treating the substrate.

17. A Group 5 metal oxide film, which is manufactured by the manufacturing method according to claim 16.

* * * * *